US006903073B2

(12) United States Patent
Habener et al.

(10) Patent No.: US 6,903,073 B2
(45) Date of Patent: Jun. 7, 2005

(54) METHODS TO STIMULATE INSULIN PRODUCTION BY PANCREATIC BETA-CELLS

(75) Inventors: Joel F. Habener, Newton Centre, MA (US); Melissa K. Thomas, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 451 days.

(21) Appl. No.: 09/733,634

(22) Filed: Dec. 8, 2000

(65) Prior Publication Data

US 2003/0013646 A1 Jan. 16, 2003

Related U.S. Application Data

(60) Provisional application No. 60/170,282, filed on Dec. 10, 1999.

(51) Int. Cl.[7] .............................................. A61K 38/00
(52) U.S. Cl. .......................... 514/12; 514/2; 530/300; 530/325
(58) Field of Search ................... 514/2, 12; 530/300, 530/325

(56) References Cited

U.S. PATENT DOCUMENTS

| 6,127,598 A | 10/2000 | German et al. |
| 6,639,051 B2 * | 10/2003 | Wang .......................... 530/350 |
| 2003/0083242 A1 * | 5/2003 | Galdes et al. .................. 514/12 |
| 2003/0162698 A1 * | 8/2003 | Galdes et al. .................. 514/12 |

FOREIGN PATENT DOCUMENTS

WO WO99/53038 10/1999

OTHER PUBLICATIONS

Kim, et al., PNAS 1998, vol. 95 pp. 13036–13041. International Search Report.
Hebrok, et al., 1998 Genes and Dev. 12:1705.
Apelqvist, et al., 1997, Curr. Biol. 7:801.

* cited by examiner

*Primary Examiner*—Christopher Tate
*Assistant Examiner*—Roy Teller
(74) *Attorney, Agent, or Firm*—Palmer & Dodge LLP; Kathleen M. Williams

(57) ABSTRACT

The invention features a method of treating deficiency of insulin in a patient, comprising administering to a patient in need thereof hedgehog protein or nucleic acid in an amount effective to raise the level of insulin in the patient.

2 Claims, 22 Drawing Sheets

```
Homo sapiens shh gene    (SEQ ID No. 13)

1 gcgaggcagc cagcgaggga gagagcgagc gggcgagccg gagcgaggaa gggaaagcgc
  61 aagagagagc gcacacgcac acacccgccg cgcgcactcg cgcccggacc cgcacgggga
 121 cagctcggaa gtcatcagtt ccatgggcga gatgctgctg ctggcgagat gtctgctgct
 181 agtcctcgtc tcctcgctgc tggtatgctc gggactggcg tgcggaccgg gcaggggggtt
 241 cgggaagagg aggcacccca aaaagctgac cccttagcc tacaagcagt ttatccccaa
 301 tgtggccgag aagaccctag gcgccagcgg aaggtatgaa gggaagatct ccagaaactc
 361 cgagcgattt aaggaactca ccccaatta caacccgac atcatattta acgatgaaga
 421 aaacaccgga gcggacaggc tgatgactca gaggtgtaag gacaagttga acgctttggc
 481 catctcggtg atgaaccagt ggccaggagt gaaactgcgg gtgaccgagg gctgggacga
 541 agatggccac cactcagagg agtctctgca ctacgagggc cgcgcagtgg acatcaccac
 601 gtctgaccgc gaccgcagca agtacggcat gctggcccgc ctggcggtgg aggccggctt
 661 cgactgggtg tactacgagt ccaaggcaca tatccactgc tcggtgaaag cagagaactc
 721 ggtggcggcc aaatcgggag gctgcttccc gggctcggcc acggtgcacc tggagcaggg
 781 cggcaccaag ctggtgaagg acctgagccc cggggaccgc gtgctggcgg cggacgacca
 841 gggccggctg ctctacagcg acttcctcac tttcctggac cgcgacgacg gcgccaagaa
 901 ggtcttctac gtgatcgaga cgcgggagcc gcgcgagcgc ctgctgctca ccgccgcgca
 961 cctgctcttt gtggcgccgc acaacgactc ggccaccggg gagcccgagg cgtcctcggg
1021 ctcggggccg ccttccgggg gcgcactggg gcctcgggcg ctgttcgcca gccgcgtgcg
1081 cccgggccag cgcgtgtacg tggtggccga gcgtgacggg gaccgccggc tcctgcccgc
1141 cgctgtgcac agcgtgaccc taagcgagga ggccgcgggc gcctacgcgc cgctcacggc
1201 ccagggcacc attctcatca acgggtgct ggcctcgtgc tacgcggtca tcgaggagca
1261 cagctgggcg cacgggcct tcgcgcctt ccgcctggcg cacgcgctcc tggctgcact
1321 ggcgcccgcg cgcacggacc gcggcggcga cagcggcggc ggggaccgcg gggcggcgg
1381 cggcagagta gccctaaccg ctccaggtgc tgccgacgct ccgggtgcgg gggccaccgc
1441 gggcatccac tggtactcgc agctgctcta ccaaataggc acctggctcc tggacagcga
1501 ggccctgcac ccgctgggca tggcggtcaa gtccagctga agccggggg ccgggggagg
1561 ggcgcgggag ggggcc
```

FIG. 1A. Homo sapiens shh gene (SEQ ID No. 13)

```
   1 gcgaggcagc cagcgaggga gagagcgagc gggcgagccg gagcgaggaa gggaaagcgc
  61 aagagagagc gcacacgcac acacccgccg cgcgcactcg cgcccggacc cgcacgggga
 121 cagctcggaa gtcatcagtt ccatgggcga gatgctgctg ctggcgagat gtctgctgct
 181 agtcctcgtc tcctcgctgc tggtatgctc gggactggcg tgcggaccgg gcagggggtt
 241 cgggaagagg aggcacccca aaaagctgac ccctttagcc tacaagcagt ttatcccaa
 301 tgtggccgag aagaccctag gcgccagcgg aaggtatgaa gggaagatct ccagaaactc
 361 cgagcgattt aaggaactca cccccaatta caacccgac atcatattta aggatgaaga
 421 aaacaccgga gcggacaggc tgatgactca gaggtgtaag gacaagttga acgctttggc
 481 catctcggtg atgaaccagt ggccaggagt gaaactgcgg gtgaccgagg gctgggacga
 541 agatggccac cactcagagg agtctctgca ctacgagggc cgcgcagtgg acatcaccac
 601 gtctgaccgc gaccgcagca agtacggcat gctggcccgc ctggcggtgg aggccggctt
 661 cgactgggtg tactacgagt ccaaggcaca tatccactgc tcggtgaaag cagagaactc
 721 ggtggcggcc aaatcgggag gctgcttccc gggctcggcc acggtgcacc tggagcaggg
 781 cggcaccaag ctggtgaagg acctgagccc cggggaccgc gtgctggcgg cggacgacca
 841 gggccggctg ctctacagcg acttcctcac ttccctggac cgcgacgacg gcgcaaagaa
 901 ggtcttctac gtgatcgaga cgcgggagcc gcgcgagcgc ctgctgctca ccgccgcgca
 961 cctgctcttt gtggcgccgc acaacgactc ggccaccggg gagcccgagg cgtcctcggg
1021 ctcggggccg ccttccgggg cgcactggg gcctcgggcg ctgttcgcca gccgcgtgcg
1081 cccgggccag cgcgtgtacg tggtggccga gcgtgacggg gaccgccggc tcctgcccgc
1141 cgctgtgcac agcgtgaccc taagcgagga ggccgcggcc gcctacgcgc cgctcacggc
1201 ccagggcacc attctcatca accgggtgct ggcctcgtgc tacgcggtca tcgaggagca
1261 cagctgggcg caccgggcct tcgcgccctt ccgcctggcg cacgcgctcc tggctgcact
1321 ggcgcccgcg cgcacggacc gcggcgggga cagcggcggc gggaccgcg ggggcggcgg
1381 cggcagagta gccctaaccg ctccaggtgc tgccgacgct ccgggtgcgg gggccaccgc
1441 gggcatccac tggtactcgc agctgttcta ccaaataggc acctggctgc tggacagcga
1501 ggccctgcac ccgctgggca tggcggtcaa gtccagctga agccgggggg ccgggggagg
1561 ggcgcgggag ggggcc
```

FIG. 1B. Homo sapiens shh polypeptide (SEQ ID No. 14)

```
MLLLARCLLLVLVSSLLVCSGLACGPGRGFGKRRHPKKLTPLAYKQFIPNVAEKTLGASGRYEGKISRNSERFKELTP
NYNPDIIFKDEENTGADRLMTQRCKDKLNALAISVMNQWPGVKLRVTEGWDEDGHHSEESLHYEGRAVDITTSDRDRS
KYGMLARLAVEAGFDWVYYESKAHIHCSVKAENSVAAKSGGCFPGSATVHLEQGGTKLVKDLSPGDRVLAADDQGRLL
YSDFLTFLDRDDGAKKVFYVIETREPRERLLLTAAHLLFVAPHNDSATGEPEASSGSGPPSGGALGPRALFASRVRPG
QRVYVAERDGDRRLLPAAVHSVTLSEEAAGAYAPLTAQGTILINRVLASCYAVIEEHSWAHRAFAPFRLAHALLAAL
APARTDRGGDSGGGDRGGGGRVALTAPGAADAPGAGATAGIHWYSQLLYQIGTWLLDSEALHPLGMAVKSS
```

FIG. 2A. Mus musculus shh gene (SEQ ID No. 15)

```
   1 atgctgctgc tgctggccag atgttttctg gtgatccttg cttcctcgct gctggtgtgc
  61 cccgggctgg cctgtgggcc cggcaggggg tttggaaaga ggcggcaccc caaaaagctg
 121 acccttttag cctacaagca gtttattccc aacgtagccg agaagaccct aggggccagc
 181 ggcagatatg aagggaagat cacaagaaac tccgaacgat ttaaggaact caccccaat
 241 tacaacccg acatcatatt taaggatgag gaaaacacgg gagcagaccg gctgatgact
 301 cagaggtgca agacaagtt aaatgccttg gccatctctg tgatgaacca gtggcctgga
 361 gtgaagctgc gagtgaccga gggctgggat gaggacggcc atcattcaga ggagtctcta
 421 cactatgagg gtcgagcagt ggacatcacc acgtccgacc gggaccgcag caagtacggc
 481 atgctggctc gcctggctgt ggaagcaggt ttcgactggg tctactatga atccaaagct
 541 cacatccact gttctgtgaa agcagagaac tccgtggcgg ccaaatccgg cggctgtttc
 601 ccgggatccg ccaccgtgca cctggagcag ggcggcacca agctggtgaa ggacttacgt
 661 cccggagacc gcgtgctggc ggctgacgac cagggccggc tgctgtacag cgacttcctc
 721 accttcctgg accgcgacga aggcgccaag aaggtcttct acgtgatcga gacgctggag
 781 ccgcgcgagc gcctgctgct caccgccgcg cacctgctct tcgtcgccgcc gcacaacgac
 841 tcggggccca cgcccgggcc aagcgcgctc tttgccagcc gcgtgcgccc cgggcagcgc
 901 gtgtacgtgg tggctgaacg cggcggggac cgccggctgc tgcccgccgc ggtgcacagc
 961 gtgacgctgc gagaggagga ggcgggcgcg tacgcgccgc tcacggcgca cggcaccatt
1021 ctcatcaacc gggtgctcgc ctcgtgctac gctgtcatcg aggagcacag ctgggcacac
1081 cgggccttcg cgcctttccg cctggcgcac gcgctgctgg ccgcgctggc acccgcccgc
1141 acggacggcg ggggcggggg cagcatccct gcagcgcaat ctgcaacgga agcgaggggc
1201 gcggagccga ctgcgggcat ccactggtac tcgcagctgc tctaccacat tggcacctgg
1261 ctgttggaca gcgagaccat gcatcccttg ggaatggcgg tcaagtccag ctga
```

FIG. 2B. Mus musculus shh polypeptide (SEQ ID No. 16)

MLLLLARCFLVILASSLLVCPGLACGPGRGFGKRRHPKKLTPLAYKQFIPNVAEKTLGASGRYEGKITRNSERFKELT
PNYNPDIIFKDEENTGADRLMTQRCKDKLNALAISVMNQWPGVKLRVTEGWDEDGHHSEESLHYEGRAVDITTSDRDR
SKYGMLARLAVEAGFDWVYYESKAHIHCSVKAENSVAAKSGGCFPGSATVHLEQGGTKLVKDLRPGDRVLAADDQGRL
LYSDFLTFLDRDEGAKKVFYVIETLEPRERLLLTAAHLLFVAPHNDSGPTPGPSALFASRVRPGQRVYVVAERGGDRR
LLPAAVHSVTLREEEAGAYAPLTAHGTILINRVLASCYAVIEEHSWAHRAFAPFRLAHALLAALAPARTDGGGGSIP
AAQSATEARGAEPTAGIHWYSQLLYHIGTWLLDSETMHPLGMAVKSS

Fig. 3A. Rattus norvegicus shh gene (SEQ ID No. 17)

```
  1 atcatattta aggatgagga aaacactgga gcagaccggc tgatgactca gaggtgcaaa
 61 gacaagttaa atgccttggc catctccgtg atgaaccagt ggcctggagt gaagcttcga
121 gtgactgagg gctgggatga ggacggccat cattcagagg agtctctaca ctatgaggt
181 cgagcagtgg acatcaccac gtctgacagg gaccgcagca agtatggcat gctggctcgc
241 ctggctgtgg aggcaggctt cgactgggtc tactatgaat ccaaagctca catccactgc
301 tctgtgaaag cagagaactc cgtggcggcc aaatctggcg gctgcttccc gggatcagcc
361 acagtgcacc tggagcaggg tggcaccaag ttagtgaagg atctaagtcc cggggaccsc
421 gtgctggcgg ctgacgacca gggccggctg ctgtacagcg acttcctcac cttcctggac
481 cg
```

FIG. 3B. Rattus norvegicus shh polypeptide (SEQ ID No. 18)

IIFKDEENTGADRLMTQRCKDKLNALAISVMNQWPGVKLRVTEGWDEDGHHSEESLHYEGRAVDITTSDRDRS:YGML
ARLAVEAGFDWVYYESKAHIHCSVKAENSVAAKSGGCFPGSATVHLEQGGTKLVKDLSPGDRVLAADDQGRLLYSDFL
TFLDR

FIG. 4A. Homo sapiens dhh gene (SEQ ID No. 19)

```
  1 atattatttt taaggatgaa gagaacagtg gagccgaccg cctgatgacc gagcgttgta
 61 aggagcgggt gaacgctttg gccattgccg tgatgaacat gtggcccgga gtgcgcctac
121 gagtgactga gggctgggac gaggacggcc accacgctca ggattcactc cactacgaag
181 gccgtgcttt ggacatcact acgtctgacc gcgaccgcaa caagtatggg ttgctggcgc
241 gcctcgcagt ggaagccggc tttgactggg tctactacgg atccg
```

FIG. 4B. Homo sapiens dhh polypeptide (SEQ ID No. 20)

```
IIFKDEENSGADRLMTERCKERVNALAIAVMNMWPGVRLRVTEGWDEDGHHAQDSLHYEGRALDITTSDRDRNKYGLL
ARLAVEAGFDWVYYGS
```

FIG. 5A. Mus musculus dhh gene (SEQ ID No. 21)

```
   1 atggctctgc cggccagtct gttgcccctg tgctgcttgg cactcttggc actatctgcc
  61 cagagctgcg ggccgggccg aggaccggtt ggccggcggc gttatgtgcg caagcaactt
 121 gtgcctctgc tatacaagca gtttgtgccc agtatgcccg agcggaccct gggcgcgagt
 181 gggccagcgg aggggagggt aacaaggggg tcggagcgct tccgggacct cgtacccaac
 241 tacaacccg acataatctt caaggatgag gagaacagcg gcgcagaccg cctgatgaca
 301 gagcgttgca aagagcgggt gaacgctcta gccatcgcgg tgatgaacat gtggcccgga
 361 gtacgcctac gtgtgactga aggctgggac gaggacggcc accacgcaca ggattcactc
 421 cactacgaag gccgtgcctt ggacatcacc acgtctgacc gtgaccgtaa taagtatggt
 481 ttgttggcgc gcctagctgt ggaagccgga ttcgactggg tctactacga gtcccgcaac
 541 cacatccacg tatcggtcaa agctgataac tcactggcgg tccgagccgg aggctgcttt
 601 ccgggaaatg ccacggtgcg cttgcggagc ggcgaacgga aggggctgag ggaactacat
 661 cgtggtgact gggtactggc cgctgatgca gcgggccgag tggtacccac gccagtgctg
 721 ctcttcctgg accgggatct gcagcgccgc gcctcgttcg tggctgtgga gaccgagcgg
 781 cctccgcgca aactgttgct cacaccctgg catctggtgt tcgctgctcg cgggccagcg
 841 cctgctccag gtgactttgc accggtgttc gcgcgccgct tacgtgctgg cgactcggtg
 901 ctggctcccg gcggggacgc gctccagccg gcgcgcgtag cccgcgtggc gcgcgaggaa
 961 gccgtgggcg tgttcgcacc gctcactgcg cacgggacgc tgctggtcaa cgacgtcctc
1021 gcctcctgct acgcggttct agagagtcac cagtgggccc accgcgcctt cgccccttg
1081 cggctgctgc acgcgctcgg ggctctgctc cctggggtg cagtccagcc gactggcatg
1141 cattggtact ctcgcctcct ttaccgcttg gccgaggagt taatgggctg a
```

FIG. 5B. Mus musculus dhh polypeptide (SEQ ID No. 22)

```
MALPASLLPLCCLALLALSAQSCGPGRGPVGRRRYVRKQLVPLLYKQFVPSMPERTLGASGPAEGRVTRGSERFRDLV
PNYNPDIIFKDEENSGADRLMTERCKERVNALAIAVMNMWPGVRLRVTEGWDEDGHHAQDSLHYEGRALDITTSDRDR
NKYGLLARLAVEAGFDWVYYESRNHIHVSVKADNSLAVRAGGCFPGNATVRLRSGERKGLRELHRGDWVLAADAAGRV
VPTPVLLFLDRDLQRRASFVAVETERPPRKLLLTPWHLVFAARGPAPAPGDFAPVFARRLRAGDSVLAPGGDALQPAR
VARVAREEAVGVFAPLTAHGTLLVNDVLASCYAVLESHQWAHRAFAPLRLLHALGALLPGGAVQPTGMHWYSRLLYRL
AEELMG
```

FIG. 6A. Rattus norvegicus dhh gene (SEQ ID No. 23)

```
  1 tctgtccaga gctgcgggcc aggccgagga ccggttggcc ggcggcgtta cgtgcgcaag
 61 caacttgtgc ctctgctcta caagcagttt gtgcctagta tgcccgagcg gacccttggc
121 gcgagtgggc cagcggaggg gagggtaaca aggggggtcgg agcgcttccg ggacctcgtc
181 cccaactaca accccgacat aatcttcaag gatgaggaga acagcggcgc tgaccgcctg
241 atgacagagc gttgcaaaga gcgggtgaat gctctagcca tcgcggtgat gaacatgtgg
301 cccggagtac gcctacgcgt gactgaaggt tgggacgagg atggccacca cgcacaggac
361 tcactgcact acgaaggccg tgccct
```

FIG. 6B. Rattus norvegicus dhh polypeptide (SEQ ID No. 24)

SVQSCGPGRGPVGRRRYVRKQLVPLLYKQFVPSMPERTLGASGPAEGRVTRGSERFRDLVPNYNPDIIFKDEENSGAD
RLMTERCKERVNALAIAVMNMWPGVRLRVTEGWDEDGHHAQDSLHYEGRAL

FIG. 7A. Homo sapiens ihh exon 1 (SEQ ID No. 25)

```
  1 atgtctcccg cccggctccg gccccgactg cacttctgcc tggtcctgtt gctgctgctg
 61 gtggtgccgg cggcatgggg ctgcgggccg ggtcgggtgg tgggcagccg ccggcgaccg
121 ccacgcaaac tcgtgccgct cgcctacaag cagttcagcc ccaatgtgcc cgagaagacc
181 ctgggcgcca gcggacgcta tgaaggcaag atcgctcgca gctccgagcg cttcaaggag
241 ctcaccccca attacaatcc agacatcatc ttcaaggacg aggagaacac aggcgccgac
301 cgcctcatga cccag
```

FIG. 7B. Homo sapiens ihh exon 2  (SEQ ID No. 26)

```
  1 cctctcccag cgctgcaagg accgcctgaa ctcgctggct atctcggtga tgaaccagtg
 61 gccggtgtg aagctgcggg tgaccgaggg ctgggacgag gacggccacc actcagagga
121 gtccctgcat tatgagggcc gcgcggtgga catcaccaca tcagaccgcg accgcaataa
181 gtatggactg ctggcgcgct tggcagtgga ggccggcttt gactgggtgt attacgagtc
241 aaaggcccac gtgcattgct ccgtcaagtc cggtgagccg ccg
```

FIG 7C. Homo sapiens ihh exon 3 (SEQ ID No. 27)

```
  1 tttctcccac agagcactcg gccgcagcca agacgggcgg ctgcttccct gccggagctc
 61 aggtacgcct ggagagtggg gcgcgtgtgg ccttgtcagc cgtgaggccg ggagaccgtg
121 tgttggccat gggggaggat gggagcccca ccttcagcga tgtgatcatt ttactggacc
181 gcgagccccca caggctgaga gcctttcagt tcatcgagac tcaggacccc ccacgccgct
241 tggcactcac acccgctcac ttgctcttta cggctgacaa tcacacggag ccggcagccc
301 gcttccgggc cacatttgcc agccacgtgc agcctggcca gtacgtgctg gtggctgtgg
361 tgccaggcct gcagcctgcc cgcgtggcag ctgtctctac acacgtggcc ctcggggcct
421 acgccccgct cacaaagcat gggacactgg tggtggagga tgtggtggca tcctgcttcg
481 cggccgtggc tgaccaccac ctggctcagt tggccttctg gccctgaga ctctttcaca
541 gcttggcatg gggcagctgg acccggggg agggtgtgca ttggtacccc cagctgctct
601 accgcctggg gcgtctcctg ctagaagagg gcagcttcca cccactgggc atgtccgggg
661 cagggagctg aaaggactcc acc
```

FIG. 7D. Homo sapiens ihh polypeptide (SEQ ID No. 28)

```
MSPARLPPRLHFCLVLLLLLVVPAAWGCPGRVVGSRRRPPPRKLVPLAYKQFSPNVPEKTLGASGRYEGKIARSSERF
KELTPNYNPDIIFKDEENTGADRLMTQRCKDRLNSLAISVMNQWPGVKLRVTEGWDEDGHHSEESLHYEGRAVDITTS
DRDRNKYGLLARLAVEAGFDWVYYESKAHVHCSVKSEHSAAAKTGGCFPAGAQVRLESGARVALSAVRPGDRVLAMGE
DGSPTFSDVIILLDREPHRLRAFQFIETQDPPRRLALTPAHLLFTADNHTEPAARFRATFASHVQPGQYVLVAGVPGL
QPARVAAVSTHVALGAYAPLTKHGTLVVEDVVASCFAAVADHHLAQLAFWPLRLFHSLAWGSWTPGEGVHWYPQLLYR
LGRLLLEEGSFHPLGMSGAGS
```

FIG. 8A. Mus musculus ihh gene (SEQ ID No. 29)

```
   1 gcggccgccg cgttgccaaa acaaacgggc cggcctattt attggcggcc ggcgagccgg
  61 gcagctcaga gtcgaggcgc cgaggggggac agcacgccgc caccagccag ggccccgggc
 121 ccccgccccg cacctgagtc ccgtcggcct tgagccgcgt cgcgctgccc atggcgcccc
 181 cgcatggagt ccccaagagc cacccagacg cctgagtccc cgaagctgtc ccagccacgc
 241 gcccacctat cagcccacca ggcgccctcg cccgctgctc tcccgggcta cccggccatg
 301 tctcccgcct ggctccggcc ccgactgcgg ttctgtctgt tcctgctgct gctgcttctg
 361 gtgccggcgg cgcggggctg cgggccgggc cgggtggtgg gcagccgccg gaggccgcct
 421 cgcaagctcg tgcctcttgc ctacaagcag ttcagcccca acgtgccgga aagaccctg
 481 ggcgccagcg ggcgctacga aggcaagatc gcgcgcagct ctgagcgctt caaagagctc
 541 accccaact acaatcccga catcatcttc aaggacgagg agaacacggg tgccgaccgc
 601 ctcatgaccc agcgctgcaa ggaccgtctg aactcactgg ccatctctgt catgaaccag
 661 tggcctggtg tgaaactgcg ggtgaccgaa ggctgggatg aagatggcca tcactcagag
 721 gagtctttac actatgaggg ccgcgcggtg gatatcacca cctcagaccg tgaccgaaat
 781 aagtatggac tgctggcgcg cttagcagtg gaggccggct tcgactgggt gtattacgag
 841 tccaaggccc acgtgcattg ctctgtcaag tctgagcatt cggccgctgc caagacaggt
 901 ggctgctttc ctgccggagc ccaggtgcgc ctagagaacg gggagcgtgt ggcctgtca
 961 gctgtaaagc caggagaccg ggtgctggcc atggggagg atgggacccc caccttcagt
1021 gatgtgctta tttcctgga ccgcgagcca aaccggctga gagcttttca ggtcatcgag
1081 actcaggatc ctccgcgtcg gctggcgctc acgcctgccc acctgctctt cattgcggac
1141 aatcatacag aaccagcagc ccacttccgg gccacatttg ccagccatgt gcaaccaggc
1201 caatatgtgc tggtatcagg ggtaccaggc ctccagcctg ctcgggtggc agctgtctcc
1261 acccacgtgg ccctcgggtc ctatgctcct ctcacaaggc atgggacact tgtggtggag
1321 gatgtggtgg cctcctgctt tgcagctgtg gctgaccacc atctggctca gttggccttc
1381 tggcccctgc gactgtttcc cagtttggca tggggcagct ggaccccaag tgagggtgtt
1441 cactggtacc ctcagatgct ctaccgcctg gggcgtctct tgctagaaga gagcaccttc
1501 catccactgg gcatgtctgg ggcaggaagc tgaagggact ctaaccactg ccctcctgga
1561 actgctgtgc tggatccaaa ggcctcctca ccaggaaggc tctggccctg aaggcacct
1621 ggcctgaggt tgtctccgtc ctctgtgcca gagtggagac accattgaga cttgaccagg
1681 ttgctgggcc ccgaaccttc atcttggtgt agagctgtga actgagctga caagcgtgtg
```

FIG. 8B. Mus musculus ihh polypeptide (SEQ ID No. 30)

```
MESPRATQTPESPKLSQPPRAHLSAHQAPSPAALPGYPAMSPAWLRPRLRFCLFLLLLLLVPAARGCPGRVVGSRRRP
PRKLVPLAYKQFSPNVPEKTLGASGRYEGKIARSSERFKELTPNYNPDIIFKDEENTGADRLMTQRCKDRLNSLAISV
MNQWPGVKLRVTEGWDEDGHHSEESLHYEGRAVDITTSDRDRNKYGLLARLAVEAGFDWVYYESKAHVHCSVKSEHSA
AAKTGGCFPAGAQVRLENGERVALSAVKPGDRVLAMGEDGTPTFSDVLIFLDREPNRLRAFQVIETQDPPRRLALTPA
HLLFIADNHTEPAAHFRATFASHVQPGQYVLVSGVPGLQPARVAAVSTHVALGSYAPLTRHGTLVVEDVVASCFAAVA
DHHLAQLAFWPLRLFPSLAWGSWTPSEGVHWYPQMLYRLGRLLEESTFHPLGMSGAGS
```

FIG. 9A. Rattus norvegicus ihh gene (SEQ ID No. 31)

```
  1 gcctcatgac ccagcgctgc aaggaccgtc tgaactcact ggccatctct gtcatgaacc
 61 agtggccggg tgtgaagctg cgggtgacgg aaggctggga tgaagacggc catcactcag
121 aggaatcttt acactatgag ggccgcgcgg tggatatcac cacctcagac cgcgaccgaa
181 ataagtacgg actactggcg cgcttagcag tggaggccgg cttcgactgg gtgtattacg
241 agtccaaggc ccacgttcat tgctctgtca agtctgagca ctcggctgct gccaagacag
301 gtggctgctt tcctgccgga gcccaggtcc acctagaaac tggggagcgt gtggccctgt
361 cagctgtgaa gccaggagac cgggtcctgg ccatggggga agatggcaac cccaccttca
421 gcgatgtgct cattttcctg gaccgtgagc caaacaggct gagagcttcc caggtcatcg
481 agactcagga tcctccacgt cggctggcac tcacgcctgc ccacctgctc ttc
```

FIG. 9B. Rattus norvegicus ihh polypeptide (SEQ ID No. 32)

LMTQRCKDRLNSLAISVMNQWPGVKLRVTEGWDEDGHHSEESLHYEGRAVDITTSDRDRNKYGLLARLAVEAGFDWVY
YESKAHVHCSVKSEHSAAAKTGGCFPAGAQVHLETGERVALSAVKPGDRVLAMGEDGNPTFSDVLIFLDREPNRLRAF
QVIETQDPPRRLALTPAHLLF

Fig 10
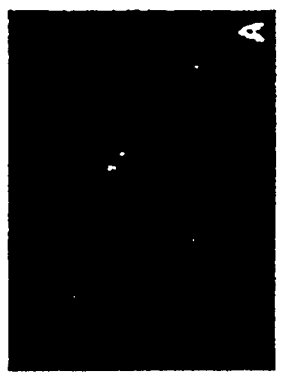

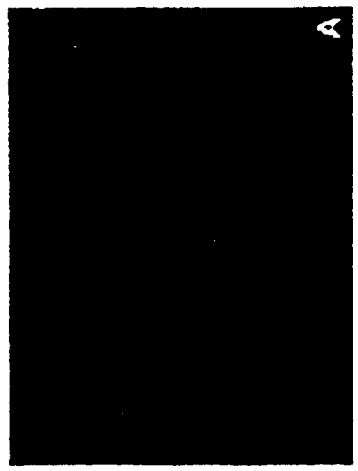
Fig. 11

Fig 12

METHODS TO STIMULATE INSULIN PRODUCTION BY PANCREATIC BETA-CELLS

This application claims the benefit of Provisional Application No. 60/170,282, filed Dec. 10, 1999.

This invention was made using U.S. government funds, and therefore, the U.S. goverment has rights in the invention

FIELD OF THE INVENTION

The invention relates to proteins useful for the treatment of diabetes mellitus.

BACKGROUND OF THE INVENTION

Morphogens are proteins, peptides, complex lipids, carbohydrates, or combinations of the above that have a role in cell, tissue and organ development. The process of tissue and organ development, either embryonic or tissue regeneration and renewal, involves a carefully orchestrated spatially and temporally orchestrated proliferation and differentiation of pleuripotential stem cells to progenitor cells that then differentiate into specific cell lineages. The specific cell lineages progress to the development of the specific complex organ systems as dictated by changing environmental cues or signals, sometimes referred to as morphogens or growth factors. The family of proteins known as hedgehog are protein morphogens. In mammals, the known hedgehog proteins include sonic hedgehog (Shh), indian hedgehog (Ihh), and desert hedgehog (Dhh). Shh has generally been found to be involved in signaling in the development of the nervous system, Ihh in limb development, chondryocyte and cartilage differentiation, and Dhh in spermatogenesis.

For example, Shh is representative of hedgehog morphogens. The bioactive signaling form (morphogen) of Shh is a protein of 18 kDA modified by the covalent attachment of cholesterol. Shh is formed from a protein precursor of 43 kDA by autoproteolysis and attachment of cholesterol by cholesterol transferase activity encoded along with the autoprotease activity in the carboxyl terminal domain of the 43 kDA precursor protein of Shh. As is typical of morphogens that act on receptors on or within their target cells, Shh acts on the cell surface receptors known as patched and smoothened, activates a signaling cascade resulting in the activation of DNA-binding transcription factors, in turn resulting in the transcriptional expression of the set of genes required to define the specific phenotype of the cells at a given stage of development. Also typical of morphogens, the cellular responses to Shh are determined by its particular ambient concentration with a concentration gradient, and the prior association of the target cells with regard to exposure to preceding morphogens and the particular time within the developmental program.

In pancreas development, Shh plays an important role in early development, in which it is the absence of Shh that is permissive for early pancreas development (Hebrok et al., 1998, Genes and Dev. 12:1705; Apelqvist et al., 1997, Curr. Biol. 7:801). It has been shown that for the patterned epithelium of the foregut tube of the chick embryo to bud into pancreatic anlages Shh must be absent (Hebrok et al., 1998, supra). It has also been shown that early overexpression of Shh in transgenic mice results in a failure of early pancreas development and a marked dysmorphogenesis in the foregut region (Apelqvist et al., 1997, supra).

SUMMARY OF THE INVENTION

The invention encompasses a method of treating deficiency of insulin in a patient, comprising administering to a patient in need thereof hedgehog protein or a modulator/activator of hedgehog signaling in an amount effective to raise the level of insulin in the patient.

The invention further encompasses a method of treating deficiency of insulin in a patient, comprising administering to a patient in need thereof a nucleic acid encoding hedgehog protein in an amount effective to raise the level of insulin in the patient.

The invention further encompasses a method of treating deficiency of insulin in a patient, comprising administering to a patient in need thereof cells expressing hedgehog protein in an amount effective to raise the level of insulin in the patient.

In the above methods, the patient may be afflicted with diabetes.

The invention also encompasses a method of stimulating insulin production in pancreatic β-cells, comprising contacting pancreatic β-cells with hedgehog protein or a modulator/activator of hedgehog signaling so as to permit insulin production from the cells.

The invention further encompasses a method of stimulating insulin production in pancreatic β-cells, comprising contacting pancreatic β-cells in vivo with hedgehog protein or a modulator/activator of hedgehog signaling so as to permit insulin production from the cells.

In the above methods, the pancreatic β-cells may be human, mouse, porcine or bovine pancreatic β-cells.

The invention further encompasses a method of modulating IDX-1 gene expression in pancreatic β-cells, comprising contacting pancreatic β-cells with hedgehog protein or a modulator/activator of hedgehog signaling in an amount effective to modulate IDX-1 gene expression.

The invention also encompasses a method of modulating IDX-1 protein in pancreatic β-cells, comprising contacting pancreatic β-cells with hedgehog protein or a modulator/activator of hedgehog signaling in an amount effective to modulate IDX-1 protein production.

The invention further encompasses a method of treating deficiency of IDX-1 in a patient, comprising administering to a patient in need thereof hedgehog protein or a modulator/activator of hedgehog signaling in an amount effective to raise the level of IDX-1 in the patient.

The invention also encompasses a method of treating deficiency of IDX-1 in a patient, comprising administering to a patient in need thereof a nucleic acid encoding hedgehog protein in an amount effective to raise the level of IDX-1 in the patient.

The invention further encompasses a method of stimulating β-cell neogenesis from β-cell pancreatic ductal precursor cells, comprising contacting β-cell pancreatic ductal precursor cells with hedgehog protein in an amount effective to stimulate neogenesis.

The invention also encompasses a method of treating deficiency of pancreatic β-cells in a patient, comprising administering to a patient in need thereof hedgehog protein in an amount effective to stimulate neogenesis from β-cell pancreatic ductal precursor cells.

The invention further encompasses a method of treating deficiency of pancreatic β-cells in a patient, comprising administering to a patient in need thereof a nucleic acid encoding hedgehog protein in an amount effective to stimulate neogenesis from β-cell pancreatic ductal precursor cells.

The invention also encompasses a method of suppressing secretion of insulin in a patient, comprising administering to a patient in need thereof an inhibitor of hedgehog protein in an amount effective to lower the level of insulin in a patient.

In a preferred embodiment, the inhibitor of hedgehog protein is cyclopamine or a derivative thereof.

In the above method, the patient may be afflicted with hyperinsulinemia.

In any of the above methods of the invention, the hedgehog protein may be of desert hedgehog, indian hedgehog, and/or sonic hedgehog protein.

DEFINITIONS

As used herein, the term "hedgehog gene" refers to any one of the nucleic acid sequences presented in FIGS. 1–9. Hedgehog protein refers to any one of the amino acid sequences presented in FIGS. 1–9. Known members of the hedgehog gene family include sonic, indian, and desert hedgehog. A hedgehog gene or protein sequence useful in the invention may vary from one of the known sequences presented in FIGS. 1–9, as long as it is at least 90% homologous at the nucleotide level over the complete gene sequence or has at least 80% sequence identity at the amino acid level over the complete amino acid sequence, and it retains the ability to stimulate insulin production in pancreatic β-cells. A hedgehog variant may include deletion, insertion, or point mutants of hedgehog. Preferably, a hedgehog variant will be able to hybridize to the polynucleotide sequences provided herein under stringent conditions. As herein used, the terms "stringent conditions" and "stringent hybridization conditions" mean hybridization occurring only if there is at least 95% and preferably at least 97% identity between the sequences, and is established via overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 micrograms/ml of denatured, sheared salmon sperm DNA, followed by washing the hybridization support in 0.1×SSC at about 65° C., as described in Sambrook, et al., Molecular Cloning: A Laboratory Manual, Second Edition, Cold Spring Harbor, N.Y., (1989), particularly Chapter 11 therein.

As used herein, a "therapeutically effective amount" with respect to hedgehog gene or protein refers to the amount of hedgehog gene or protein that is necessary to restore the level of insulin in the body to a normal level.

As used herein, a "normal" or "effective" level of endogenous insulin in a patient refers to the level of insulin produced endogenously in a healthy patient, i.e., a patient who is not afflicted with diabetes mellitus; i.e., in the range of 2–20 microUnits/ml during fasting and 50–100 microUnits/ml during non-fasting. This amount may vary in each healthy individual but it will be an amount sufficient to avoid the symptoms of diabetes mellitus. The normal levels of insulin often are indicated by a normal level of glucose in the blood under fasting conditions, i.e. a plasma glucose value of 70–110 mg/dL, and thus a variance from the normal amount of blood sugar also may be used to indicate whether a normal amount of insulin is produced.

As used herein, "diabetes mellitus type 1" refers to insulin-dependent diabetes mellitus, and "diabetes mellitus type 2" refers to non-insulin dependent diabetes mellitus. The symptoms of diabetes mellitus type 1 include hyperglycemia, glycosuria, deficiency of insulin, polyuria, polydypsia, ketonuria, and/or rapid weight loss. The symptoms of diabetes mellitus type 2 include those of type 1 as well as insulin resistance.

As used herein, "stimulation of insulin production" refers to expression of the insulin gene, insulin synthesis, and/or insulin secretion by pancreatic β-cells.

As used herein, "deficiency of insulin" refers to the reduced levels, e.g. up to 90%, 80%, 70%, 60%, 50%, 40%, 30%, 20% or 10% of normal, whether constant or varying over time, of insulin associated with patients that have diabetes mellitus (which is also characterized by symptoms including hyperglycemia, glycosuria, polyuria, polydypsia, ketonuria, insulin resistance, and/or rapid weight loss) as compared to the levels of insulin produced endogenously in a healthy patient, i.e., a patient who is not afflicted with diabetes. A deficiency of insulin may be indicated by the range of 2–20 microUnits/ml insulin for a patient under non-fasting conditions, or by a fasting plasma glucose value of $\geq$140 mg/dL, or an oral glucose tolerance test plasma glucose value of $\geq$200 mg/dL, or an elevated blood hemoglobin $A_1C(HgA_1C)$ of $\geq$6.4%.

As used herein, "suppress insulin production" or "suppression of insulin production" refers to expression of the insulin gene, insulin synthesis, and/or insulin secretion by pancreatic β-cells.

As used herein, "hyperinsulinemia" refers to the elevated levels, e.g. up to 110%, 125%, 150%, 175%, 200% or more of normal, whether constant or varying over time, of insulin associated with patients that have hyperinsulinemic conditions as compared to the levels of insulin produced endogenously in a healthy patient, i.e., a patient who is not afflicted with hyperinsulinemia. Hyperinsulinemia is typically accompanied by the metabolic condition hypoglycemia, which is associated with symptoms that may include confusion, impaired mental awareness, intense sensations of hunger, headache, dizziness, and tachycardia, while severe prolonged hypoglycemia may lead to loss of consciousness or coma. An elevated level of insulin may be indicated by the range of 21 to 2000 microUnits insulin/ml for a patient under fasting conditions, or by a fasting plasma glucose value of 30 to 60 mg/dl.

As used herein, "β-cells" refer to the fully differentiated insulin-producing β-cells of the islets of Langerhans in the pancreas. Pancreatic β-cells are characterized by their secretion of insulin and typically by their cell surface expression of the islet amyloid polypeptide (IAPP).

As used herein, "stimulation of IDX-1 production" refers to expression of the IDX-1 gene and/or IDX-1 protein synthesis by pancreatic β-cells.

As used herein, "IDX-1" refers to the gene which also has the synonyms/acronyms IPF-1, PDX-1, IUF-1, GSF-1, and STF-1.

As used herein, "β-cell neogenesis" refers to the process of the differentiation of new β-cells from pancreatic ductal precursors.

Further features and advantages of the invention will become more fully apparent in the following description of the embodiments and drawings thereof, and from the claims.

BRIEF DESCRIPTION OF DRAWINGS

FIG. 1A shows the sequence of the Homo sapiens Shh cDNA.

FIG. 1B shows the sequence of the Homo sapiens Shh coding sequence.

FIG. 2A shows the sequence of the Mus musculus Shh cDNA.

FIG. 2B shows the sequence of the Mus musculus Shh coding sequence.

FIG. 3A shows a partial sequence of the Rattus norvegicus Shh cDNA.

FIG. 3B shows a partial sequence of the Rattus norvegicus Shh coding sequence.

FIG. 4A shows a partial sequence of the Homo sapiens Dhh cDNA.

FIG. 4B shows a partial sequence of the Homo sapiens Dhh coding sequence.

FIG. 5A shows the sequence of the Mus musculus Dhh cDNA.

FIG. 5B shows the sequence of the Mus musculus Dhh coding sequence.

FIG. 6A shows a partial sequence of the Rattus norvegicus Dhh cDNA.

FIG. 6B shows a partial sequence of the Rattus norvegicus Dhh coding sequence.

FIG. 7A shows the sequence of the Homo sapiens Ihh exon 1.

FIG. 7B shows the sequence of the Homo sapiens Ihh exon 2.

FIG. 7C shows the sequence of the Homo sapiens Ihh exon 3.

FIG. 7D shows the sequence of the Homo sapiens Ihh coding sequence.

FIG. 8A shows the sequence of the Mus musculus Ihh cDNA.

FIG. 8B shows the sequence of the Mus musculus Ihh coding sequence.

FIG. 9A shows a partial sequence of the Rattus norvegicus Ihh cDNA.

FIG. 9B shows a partial sequence of the Rattus norvegicus Ihh coding sequence.

FIG. 10A shows results of immunohistochemistry of patched proteins in mouse pancreas cells.

FIGS. 10B, 10D show results of immunohistochemistry of insulin in mouse pancrease cells.

FIG. 10C shows results of immunohistochemistry of smoothened proteins in mouse pancreas cells.

FIG. 11A shows results of immunohistochemistry of patched proteins in rat INS-1 cells.

FIGS. 11B, 11D show results of immunohistochemistry of insulin rat INS-1 cells.

FIG. 11C shows results of immunohistochemistry of smoothened proteins in rat INS-1 cells.

FIG. 12 shows results of Southern blot analysis of RT-PCR products of patched RNA, smoothened RNA, indian hedgehog RNA, and desert hedgehog RNA in rat INS-1 cells and rat islet cells.

DESCRIPTION

Figure 13:
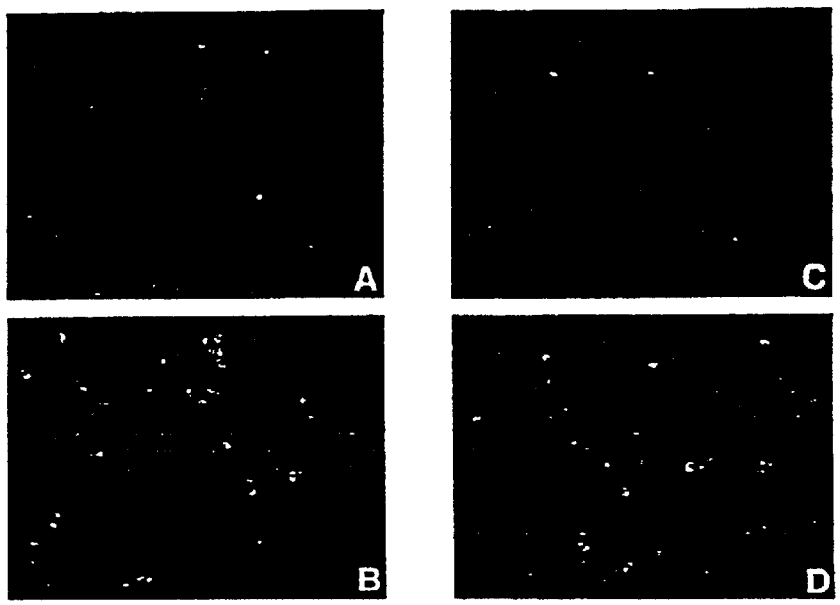
FIG. 13A shows results of immunohistochemistry of Ihh proteins in rat INS-1 cells.
FIGS. 13B, 13D show results of immunohistochemistry of insulin in rat INS-1 cells.
FIG. 13C shows results of immunohistochemistry of Dhh proteins in rat INS-1 cells.

The invention is based on the discovery that hedgehog protein is effective in fully differentiated, adult pancreatic β-cells to stimulate insulin gene expression, insulin production, insulin secretion, and IDX-1 expression.

Hedgehog Nucleotide and Amino Acid Sequences Useful in the Invention

DNA encoding hedgehog protein may be cDNA or genomic DNA. As known in the art, cDNA sequences have the arrangement of exons found in processed mRNA, forming a continuous open reading frame, while genomic sequences may have introns interrupting the open reading frame. The term "hedgehog gene" shall be intended to mean the open reading frame encoding such specific hedgehog polypeptides but not adjacent 5' and 3' non-coding nucleotide sequences involved in the regulation of expression; the latter sequences are called hedgehog regulating sequences that are operatively associated with the gene in its native state or are operative in a recombinant state useful in the invention. The mammalian hedgehog family consists of sonic (Shh), indian (Ihh), and desert (Dhh) hedgehog proteins or other members of the hedgehog family as yet not identified or discovered. The known genes and gene products (also referred to as coding sequence) are provided below for the human, mouse and rat hedgehogs.

Complete sequences are available for the gene products of the human and mouse Shh genes, while a partial sequence is available for the rat Shh. The gene sequence for the human Shh, GenBank Accession No. L38518, is shown in FIG. 1A, and its gene product, corresponding to nucleotides 152–1540, is provided in FIG. 1B. The gene sequence for the mouse Shh, GenBank Accession No. X76290, is given in FIG. 2A, and its coding sequence, encoded by the entire sequence of nucleotides 1–1314, is provided in FIG. 2B. A partial gene sequence of the rat Shh, GenBank Accession No. AF162915, is shown in FIG. 3A and the corresponding partial coding sequence based on translation of nucleotides 1–482 is presented in FIG. 3B.

The available sequences of mammalian Dhh proteins include partial coding sequences for rat and human Dhh, and a complete sequence for mouse Dhh. The partial human Dhh gene, GenBank Accession No. U59748, and coding sequences (translated from nucleotides 1–285) are shown in FIGS. 4A and 4B, respectively. The gene sequence from the mouse Dhh mRNA, GenBank Accession No. U59748, is presented in FIG. 5A and its corresponding gene product, corresponding to nucleotides 1–1491, is given in FIG. 5B. The partial rat Dhh gene sequence, GenBank Accession No. AF148226, and coding region (translated from nucleotides 1–386) are shown in FIGS. 6A and 6B, respectively.

The sequences available for the Ihh proteins include a complete coding sequence for human Ihh derived from three exons, a complete sequence for mouse Ihh, and a partial coding sequence for rat Ihh. The sequences for the human Ihh exon 1 (GenBank Accession No. AB010092), exon 2 (GenBank Accession No. AB018075), and exon 3 (GenBank Accession No. AB018076) are respectively provided in FIGS. 7A, 7B, and 7C. The complete coding sequence for human Ihh (from GenBank Accession No. AB018076), corresponding to the sequence derived by contiguously joining nucleotides 1–315 of exon 1, 11–272 of exon 2, and 13–671 of exon 3, is shown in FIG. 7D. The mouse Ihh gene sequence, GenBank Accession No. U85610, is given in FIG. 8A, and its corresponding gene product, translated from nucleotides 184–1533, is shown in FIG. 8B. The partial rat Ihh gene sequence, GenBank Accession No. AF162914, is given in FIG. 9A and its translated partial coding sequence (from nucleotides 1–533) is provided in FIG. 9B.

Hedgehog Nucleic Acid Isolation

The hedgehog sequence information provided above can be used to obtain nucleic acid encoding a hedgehog gene through a number of methods familiar to those of skill in the art. For instance, nucleic acid encoding a hedgehog gene can be amplified from a complementary DNA (cDNA) library with the polymerase chain reaction (PCR). In this case, synthetic oligonucleotide primers directed to the 5' and 3' ends of a given hedgehog sequence can be generated based on the sequence data provided. The primers can then be used in conjunction with a cDNA library, which can be purchased from commercial suppliers such as Stratagene (La Jolla, Calif.), to amplify a cDNA sequence between and including the primer sequences, thereby providing the nucleic acid encoding a hedgehog gene from a cDNA library. The amplified cDNA can then be cloned into any of a number of plasmid vectors, such as those that enable protein expression or the generation of nucleic acids that can be used as probes for nucleic acids that encode hedgehog. Once cloned into a plasmid vector, a substantial quantity of the nucleic acid encoding a hedgehog gene can be obtained by propagation of the vector according to conventional techniques.

As briefly described, cDNA corresponding to a hedgehog gene can be isolated for human hedgehog as described by Marigo et al., 1995, Genomics 28:441 (herein incorporated by reference), in which two human hedgehog homologs, Shh and Ihh, were cloned. Sequence comparison of several hedgehog genes, including mouse Shh, Ihh, and Dhh, and chick Shh (GenBank Accession No. L28099) showed that several regions within the second exon are apparently invariant among genes of this family. Degenerate oligonucleotides directed to these regions are used to amplify human genomic DNA by nested PCR. The expected 220-bp PCR product is subcloned into pGEM7zf (Promega, Madison, Wis.) and sequenced using Sequenase v2.0 (U.S. Biochemicals, Cleveland, Ohio). A clone displaying high nucleotide similarity to mouse Ihh and mouse Shh sequences (Echelard, et al., 1993, Cell 75: 1417) is used for screening a human fetal lung 5'-stretch plus cDNA library (Clontech, Palo Alto, Calif.) in λgt10 phage. The library is screened following the protocol suggested by the company, and positive plaques are identified, purified, subcloned into pBluescript SK(+) (Stratagene, La Jolla, Calif.), and sequenced, identifying them as the human homologues of Shh and Ihh.

Hedgehog Protein Synthesis

The hedgehog gene sequences provided above may be employed to produce the hedgehog proteins of the invention. These proteins include intact hedgehog, or an active fragment thereof, since the bioactive signaling form of hedgehog may be derived by proteolysis of a protein precursor, as is the case for Shh. According to methods familiar to those of skill in the art, nucleic acid encoding the gene is cloned into an appropriate vector (such as described above) so that it may be expressed, and the protein is then produced by expression of the gene and subsequent purification of the expressed protein. For expression, an expression cassette may be employed, providing for a transcriptional and translational initiation region, which may be inducible or constitutive, the coding region under the transcriptional control of the transcriptional initiation region, and a transcriptional and translational termination region. Various transcriptional initiation regions may be employed which are functional in the expression host.

The peptide may be expressed in prokaryotes or eukaryotes by conventional techniques, depending upon the purpose for expression. For large scale production of the protein, a unicellular organism may be used as the expression host, such as E. coli, B. subtilis, and S. cerevisiae. Alternatively, cells of a multicellular organism, e.g. eukaryotes such as vertebrates, particularly mammals, may be used as the expression host. In many situations, it may be desirable to express the subject hedgehog gene in a mammalian host cell, whereby the hedgehog gene product is cholesterolated, and secreted.

With the availability of the protein in large amounts by employing an expression host, the protein may be isolated and purified by conventional techniques. A lysate may be prepared of the expression host and the lysate purified using HPLC, exclusion chromatography, gel electrophoresis, affinity chromatography, or other purification techniques. The purified protein will generally be at least about 80% pure, preferably at least about 90% pure, and may be up to and including 100% pure. By pure is intended free of other proteins, as well as of cellular debris.

For illustrative purposes, Shh protein can be made from mammalian sources such as mouse L-cells or yeast, as briefly described below, according to Katsuura et al., 1999, FEBS Letters 447:325. To express mouse Shh in mouse L-cells, a cDNA encoding the mouse Shh is amplified by PCR from the full length mouse Shh cDNA, and cloned into an appropriate L-cell expression vector. The resulting plasmid is transfected into mouse fibroblastic L-cells using lipofectamine reagent (Gibco BRL, Gaithersburg, Md.). These transfectants carrying high number of copies of expression plasmid are selected with 800 μg/ml G418

(Gibco BRL) in Dulbecco's modified Eagle's medium (DMEM, Gibco BRL) supplemented with 10% fetal bovine serum (FBS, purchased from Gibco BRL). The transfectants are then cultured in DMEM supplemented with 0.5% FBS and 800 µg/ml G418 for 3 or 4 days and the culture supernatants are collected by centrifugation at 3000 rpm and for 10 min. and then filtered through a 0.22 µm filter.

To express mouse Shh in yeast, an expression vector of mouse Shh is constructed by amplifying the Shh cDNA from a mouse cDNA library by PCR and the product is cloned into a pPIC9K vector (Invitrogen, Carlsbad, Calif.). Transformants are obtained by introducing each vector into spheroplasts of *Pichia pastoris* KM71 (arg4 his4 aoxl:ARG4), followed by selection on YPD agar plates (Difco Laboratories, Detroit, Mich.) with 0.5–20 mg/ml G418. To express the protein, the clones are pre-cultured in BMG liquid media (Difco Laboratories) at 30° C. for 18 h., transferred to BMMY media (Difco Laboratories) to give an $A_{650}$ of about 1.0 and induced by the addition of methanol to a final concentration of 0.5% every 24 h. according to the instruction manual of Invitrogen. Cells are harvested 45 h. after induction.

To purify the recombinant proteins expressed in either L-cells or yeast, the culture supernatants are applied to a HiTrap SP (sulphopropyl) column (Amersham Pharmacia biotech, Uppsala, Sweden), previously equilibrated with 20 MM sodium phosphate buffer (PB), pH 7.4, containing 50 mM NaCl. After washing the column with the same buffer, the proteins are eluted with 1 M NaCl in PB, pH 7.4. Eluates of the SP column are further purified by gel filtration using Superdex 200 pg, 1.6/60 cm (Amersham Pharmacia biotech) with 150 mM NaCl in PB. The fractions containing Shh are pooled and concentrated with Centriprep-10 (Amicon, Bedford, Mass.). The protein concentration is determined by the BCA (bicinchoninic acid) protein assay kit (Pierce, Milwaukee, Wis.)

Diabetes Treatment Methods According to the Invention

Methods of the invention include hedgehog administration in the form of hedgehog protein, nucleic acids encoding, a vector containing a hedgehog gene (gene therapy), cells expressing hedgehog protein, and tissue which produces hedgehog protein. In each case of hedgehog administration, hedgehog is delivered to the patient afflicted with diabetes mellitus in an amount sufficient to provide an effective level of endogenous insulin in the patient. An "effective" or "normal" level of endogenous insulin in a patient refers generally to that level of insulin that is produced endogenously in a healthy patient, i.e., a patient who is not afflicted with diabetes. Alternatively, an "effective" level may also refer to the level of insulin that is determined by the practitioner to be medically effective to alleviate the symptoms of diabetes.

Dosage and Mode of Administration of Protein According to the Invention

Methods of the invention include administering hedgehog protein or a variant thereof. Thus, according to the invention, a diabetic patient may be treated by administering to a patient afflicted with diabetes hedgehog protein, or a variant thereof. Optimally, the protein is administered in a pharmaceutically acceptable vehicle, and is administered in an amount sufficient to provide an effective level of endogenous insulin in the patient.

The patient may be treated with intact hedgehog protein, or an active fragment thereof, particularly a cleaved fragment as generated by normal processing. Desirably, the peptides will not induce an immune response, particularly an antibody response. Xenogeneic analogs may be screened for their ability provide a therapeutic effect, most advantageously, without raising an immune response.

Various methods for administration may be employed. The polypeptide formulation may be given orally, or may be injected intravascularly, subcutaneously, peritoneally, and so forth. The dosage of the therapeutic formulation will vary widely, depending upon the frequency of administration, the manner of administration, and the clearance of the agent from the patient. For example, the dose may range from 1 to 10 mg hedgehog protein/kg body weight. The initial dose may be larger, followed by smaller maintenance doses. The dose may be administered as infrequently as weekly or biweekly, or fractionated into smaller doses and administered daily, semi-weekly, etc. to maintain an effective dosage level. In many cases, oral administration will require a higher dose than if administered intravenously.

The hedgehog peptides may be prepared as formulations at a pharmacologically effective dose in pharmaceutically acceptable media, for example normal saline, PBS, etc. The additives may include bacteriocidal agents, stabilizers, buffers, or the like. To enhance the half-life of the subject peptide or subject peptide conjugates, the peptides may be encapsulated, introduced into the lumen of liposomes, prepared as a colloid, or another conventional technique may be employed that provides for an extended lifetime of the peptides.

Dosage and Mode of Administration of Nucleic Acids According to the Invention

In addition to administering hedgehog protein, another means of administration according to the invention is administration of DNA encoding hedgehog or its variant. Thus, according to the invention, diabetes mellitus type 1 may be treated by administering to a patient afflicted with diabetes nucleic acid encoding hedgehog or a variant thereof. The nucleic acid will optimally be carried by a vehicle, and is administered in numbers sufficient to provide an effective level of endogenous insulin in a patient.

The administration of nucleic acids encoding hedgehog to treat diabetes is an application of gene therapy, which involves the direct manipulation and use of genes to treat disease. A hedgehog gene may be delivered to a target cell with relatively high specificity and efficiency according to methods known in the art. Target cells useful according to the invention will include, but not be limited to, pancreatic cells, e.g., non-islet pancreatic cells, pancreatic islet cells, islet cells of the β-cell type, non-β-cell islet cells, and pancreatic duct cells. There are multiple ways to deliver and express genes as part of a gene therapy protocol. Typically, a nucleic acid of interest will be propagated and carried on an episomal vector.

The following gene therapy methods are representative of gene therapy methods useful for accomplishing gene therapy according to the invention, and are not limiting to the invention.

An episomal vector containing the therapeutic hedgehog gene or variants thereof (herein, an episomal vector containing the hedgehog gene will be referred to as the hedgehog vector) can be administered to patients having diabetes or a deficiency of insulin treatable by supplying and expressing the hedgehog gene, e.g., by exogenous delivery of a naked hedgehog vector, a hedgehog vector associated with specific carriers, by means of an appropriate delivery vehicle, e.g., a liposome, by use of iontophoresis, electroporation and other pharmacologically approved methods of delivery. Routes of administration may include intramuscular, intravenous, aerosol, oral (tablet or pill form), topical, systemic, ocular, as a suppository, intraperitoneal and/or intrathecal.

There are multiple ways to deliver genes as part of a gene therapy protocol. At least three types of delivery strategies are useful in the present invention, including: injection of naked hedgehog vector, or injection of charge modified hedgehog vector, or particle carrier drug delivery vehicles. Unmodified nucleic acid encoding the hedgehog vector, like most small molecules, are taken up by cells, albeit slowly. To enhance cellular uptake, the hedgehog vector may be modified in ways which reduce its charge but will maintain the expression of specific functional groups in the final translation product. This results in a molecule which is able to diffuse across the cell membrane, thus removing the permeability barrier.

Chemical modifications of the phosphate backbone may be used to reduce the negative charge allowing free diffusion across the membrane. In the body, maintenance of an external concentration of the hedgehog vector relative to the pancreas will be necessary to drive the diffusion of the modified hedgehog vector into the β-cells of the pancreas. Administration routes which allow the pancreas to be exposed to a transient high concentration of the nucleic acid encoding a hedgehog vector which is slowly dissipated by systematic adsorption are preferred. Intravenous administration with a drug carrier designed to increase the circulation half-life of the hedgehog vector can be used. The size and composition of the drug carrier restricts rapid clearance from the blood stream. The carrier, made to accumulate at the desired site of transfer, can protect the hedgehog vector from degradative processes.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

The nucleic acid sequence encoding a hedgehog vector may also be systemically administered. Systemic absorption refers to the accumulation of drugs in the blood stream followed by distribution throughout the entire body. A gene gun may also be utilized to administer a hedgehog vector. Administration of DNA-coated microprojectiles by a gene gun requires instrumentation but is as simple as direct injection of DNA. A construct bearing the gene of interest is precipitated onto the surface of microscopic metal beads. The microprojectiles are accelerated with a shock wave or expanding helium gas, and penetrate tissues to a depth of several cell layers. This approach permits the delivery of foreign genes to the skin of anesthetized animals. This method of administration achieves expression of transgenes at high levels for several days and at detectable levels for several weeks. Each of these administration routes exposes the hedgehog vector to the targeted pancreas. Subcutaneous administration drains into a localized lymph node which proceeds through the lymphatic network into the circulation. The rate of entry into the circulation has been shown to be a function of molecular weight or size. The use of a liposome or other drug carrier localizes the hedgehog vector at the lymph node. The hedgehog vector can be modified to diffuse into the cell, or the liposome can directly participate in the delivery of either the unmodified or modified hedgehog vector to the cell. Liposomes injected intravenously show accumulation in the liver, lung and spleen. The composition and size can be adjusted so that this accumulation represents 30% to 40% of the injected dose. The remaining dose circulates in the blood stream for up to 24 hours.

The dosage will depend upon the disease indication and the route of administration but should be between 1–1000 μg hedgehog vector/kg of body weight/day. The duration of treatment will extend through the course of the disease symptoms, possibly continuously. The number of doses will depend upon disease delivery vehicle and efficacy data from clinical trials.

Dosage and Mode of Administration of Cells According to the Invention

Another means of administration according to the invention entails administering cells that secrete hedgehog protein. Thus, according to the invention, patients that have diabetes mellitus may be treated by administering cells secreting hedgehog protein or a variant thereof. The cells are administered in numbers sufficient to provide an effective level of endogenous insulin in a patient.

In this approach, cells would be cultured in vitro and transfected with nucleic acids encoding a vector containing the hedgehog gene. The cell type used would be limited to those that would be compatible with systemic administration in patients, and thus presumably would be human cells, preferably those cultured from the patient to receive the administration. The cells would be transfected with the nucleic acid encoding a hedgehog vector by means known in the art. The cells would then express the transfected hedgehog gene, producing hedgehog protein that could then be secreted. Secretion could be directed by native hedgehog signals, or alternatively by a recombinant secretion signal. In the latter instance, the vector containing the hedgehog gene can be constructed to contain a recombinant hedgehog gene that is fused with a gene encoding a secretion signal peptide appropriate for the cell type used, such that the signal will direct secretion of the hedgehog protein out of the cell. Transfection of the cells can be monitored in several ways, including examining samples of the growth media with antibodies to hedgehog. After cells are successfully transfected with hedgehog, they can be prepared for systemic administration to patients. To prepare cells for administration, they can be washed free of growth media, and placed in an appropriate pharmaceutically-acceptable media that is both compatible for the cells and the host patient.

Cells useful according to the invention will include, but not be limited to, pancreatic cells, e.g., non-islet pancreatic cells, pancreatic islet cells, islet cells of the β-cell type, non-β-cell islet cells, and pancreatic duct cells. These cell types may be isolated according to methods known in the art for ex vivo manipulation. See, e.g., Githens, 1988, Jour. Pediatr. Gastroenterol. Nutr. 7:486; Warnock et al., 1988, Transplantation 45:957; Griffin et al., 1986,Brit. Jour. Surg. 73:712; Kuhn et al., 1985, Biomed. Biochim. Acta 44:149; Bandisode, 1985, Biochem. Biophys. Res. Comm. 128:396; Gray et al., 1984, Diabetes 33:1055, all of which are hereby incorporated by reference.

As briefly described, cells expressing hedgehog can be obtained in a manner similar to that described by Fan et al., 1997, Nature Medicine 3:788, in which human keratinocytes were transfected to express sonic hedgehog. For therapeutic administration of hedgehog, the preferred cells include but are not limited to pancreatic cells, e.g., non-islet pancreatic cells, pancreatic islet cells, islet cells of the β-cell type, non-β-cell islet cells, and pancreatic duct cells. A Shh-IRES (internal ribosome entry site)-GFP (green fluorescence protein) retroviral expression vector can be generated as an aid to rapid confirmation of transduction efficiency. The full-length human Shh cDNA (Marigo et al., 1995, Genomics 28:44) without 3' polyadenylation signals (HindIII to XbaI fragment) and 610 bp IRES sequence (XbaI and SacII fragment from pGEM5Zf+, Promega, Madison, Wis.) are first subcloned into HindIII and SacII sites of pEGFP-1 (Clontech, Palo Alto, Calif.). The pShh-IRES-GFP fragment is digested with NotI and partially with BglII, and subcloned into BamHI and NotI sites of LZRS (Kinsell and Nolan G. P., 1996, Hum. Gene Ther. 7:1405), a retroviral expression plasmid. A control vector expressing only the green fluorescence protein (GFP) is produced by subcloning the BamHI and NotI fragment of EGFP from pEGFP into the BamHI and NotI sites of LZRS. Amphotropic retrovirus is produced as previously described (Kinsell and Nolan, 1996, supra; Choate et al., 1996, Hum. Gene Ther. 7:2247). β-cells are either untreated as a control or transduced with retroviral expression vectors for Shh-IRES-GFP or GFP as previously described (Choate et al., 1996, supra). Fluorescence and phase-contrast microscopy is performed with a Zeiss axiophot fluorescence microscope (Zeiss, Jena, Germany) to examine gene transfer efficiency to β-cells in vitro with the Shh-IRES-GFP retroviral expression vector.

To ensure expression of Shh in the transfected β-cells, the expression of Shh can be analyzed in vitro. Western blot analysis can be carried out to examine expression of Shh protein. For the Western blot analysis, whole-cell extracts are made from transduced and control β-cells and analyzed simultaneously with antibodies to human Shh as well as to B220 (CD45R) for an internal control. Approximately 20 μg of cell extract is analyzed by Western blotting. For examination of gene expression, mRNA is purified from whole-cell extracts and digested with deoxyribonuclease I (DNase I; Gibco BRL, Gaithersburg, Md.) to remove any contaminating genomic DNA. Reverse transcriptase polymerase chain reaction analysis is then performed with primers directed to Shh, and is internally controlled by examining expression of B220 by inclusion of B220 primers in all reactions.

Patients afflicted with diabetes can be treated with cells that secrete hedgehog by administering the cells systemically in a pharmaceutically acceptable carrier. The dosage of the therapeutic cells will vary widely from about $1\times10^3$ to $1\times10^7$ cells per individual, depending upon the hedgehog expression levels of the cells, the frequency of administration, the manner of administration, and the clearance of the agent from the patient. The initial dose may be larger, followed by smaller maintenance doses. The dose may be administered as infrequently as weekly or biweekly, or fractionated into smaller doses and administered daily, semi-weekly, etc. to maintain an effective dosage level that provides an effective level of endogenous insulin in the patient.

Dosage and Mode of Administration of Tissue According to the Invention

Another means of administration according to the invention is implantation of tissue expressing hedgehog protein. Therefore, patients that have diabetes mellitus type 1 are treated by administering tissue that provides hedgehog protein or a variant thereof. The tissue is administered in an amount sufficient to provide an effective level of endogenous insulin in a patient.

To obtain tissue expressing hedgehog protein, an ex vivo approach is utilized, whereby pancreatic tissue is removed from a patient and administered a vector encoding a hedgehog gene so that the cells of the tissue express hedgehog protein. The tissue is then re-implanted into the patient (e.g., as described by Wilson, 1992, Hum. Gene Ther. 3:179) incorporated herein by reference.

Pancreatic tissue is removed from the patient by standard surgical techniques. The tissue is then maintained by placing it in a vessel having a three dimensional geometry which approximates the in vivo gross morphology of the tissue with a solution of extracellular matrix components, similar to methods disclosed in the patent by Vandenburgh (U.S. Ser. No. 5,869,041), herein incorporated by reference, until hedgehog vector is incorporated into cells of the tissue.

Production of hedgehog protein is mediated by hedgehog vector introduced into the pancreatic tissue that allows the pancreatic cells to express hedgehog protein. The hedgehog vector is delivered to the pancreatic tissue by known means such as those used in gene therapy, as described above. Accordingly, the pancreatic tissue is administered about 1–1000 ng hedgehog vector/gm of tissue weight. The hedgehog protein encoded by the DNA is produced by the cells and liberated from the organized tissue.

To administer the tissue that delivers hedgehog protein to a patient afflicted with diabetes mellitus type 1, the tissue is implanted by standard laboratory or surgical techniques at a desired anatomical location within the patient. For example, the organized tissue is re-implanted into pancreas at the site from which it was removed or alternatively, adjacent to the pancreas. While the tissue can be temporarily implanted, it is preferred to permanently implant the organized tissue so as to provide a continuous stimulation of insulin production by hedgehog protein.

Animal Models of Diabetes Mellitus

Treatments for diabetes mellitus type that result in relief of its symptoms are tested in an animal which exhibits symptoms of diabetes, such that the animal will serve as a model for agents and procedures useful in treating diabetes in humans. Potential treatments for diabetes can therefore be first examined in the animal model by administering the potential treatment to the animal and observing the effects, and comparing the treated animals to untreated controls.

The non-obese diabetic (NOD) mouse is an important model of type 1 or insulin dependent diabetes mellitus and is a particularly relevant model for human diabetes (see Kikutano and Makino, 1992, Adv. Immunol. 52:285 and references cited therein). The development of type 1 diabetes in NOD mice occurs spontaneously and suddenly without any external stimuli. As NOD mice develop diabetes, they undergo a progressive destruction of β-cells which is caused by a chronic autoimmune disease. The development of insulin-dependent diabetes mellitus in NOD mice can be divided roughly into two phases: initiation of autoimmune insulitis (lymphocytic inflammation in the pancreatic islets) and promotion of islet destruction and overt diabetes. Diabetic NOD mice begin life with euglycemia, or normal blood glucose levels, but by about 15 to 16 weeks of age the NOD mice start becoming hyperglycemic, indicating the destruction of the majority of their pancreatic β-cells and the corresponding inability of the pancreas to produce sufficient insulin. In addition to insulin deficiency and hyperglycemia, diabetic NOD mice experience severe glycosuria, polydypsia, and polyuria, accompanied by a rapid weight loss (Kikutano and Makino, 1992, supra). Thus, both the cause and the progression of the disease are similar to human patients afflicted with insulin dependent diabetes mellitus. Spontaneous remission is rarely observed in NOD mice, and these diabetic animals die within 1 to 2 months after the onset of diabetes unless they receive insulin therapy.

The NOD mouse is used as an animal model to test the effectiveness of the various methods of treatment of diabetes by administering hedgehog protein or gene. As such, treatment via administration of hedgehog protein, nucleic acids encoding a vector containing a hedgehog gene (gene therapy), cells expressing hedgehog protein, and tissue which produces hedgehog protein are tested in the NOD mouse for their effect on type 1 diabetes.

The NOD mouse is administered hedgehog protein or gene, typically intraperitoneally, according to the following dosage amounts. For hedgehog protein, 0.5 mg protein/mouse is administered. DNA encoding hedgehog is delivered in the amount of 10–100 ng episomal hedgehog vector/mouse/day. For cell therapy, NOD mice are administered about $1\times10^1$ to $1\times10^4$ cells per mouse. Administration of hedgehog via hedgehog protein, hedgehog vector, or cell therapy is started in the NOD mice at about 4 weeks of age, and is continued for 8 to 10 weeks. As noted above, gene therapy is administered daily, while protein and cell therapies are administered 3 times a week. To administer NOD mice hedgehog via tissue that produces hedgehog protein, pancreatic tissue is removed from the mice at 4 weeks of age, transfected with about 0.1 to 1 ng hedgehog vector, and re-implanted after the allotted time required for the tissue to begin expressing hedgehog protein. The mice are monitored for diabetes beginning at about 13 weeks of age, being tested twice per week according to the methods described below. The effects of treatment are determined by comparison of treated and untreated NOD mice.

The effectiveness of the treatment methods of the invention on diabetes in the NOD mice is monitored by assaying for diabetes in the NOD mice by means known to those of skill in the art, including examining the NOD mice for polydipsia, polyuria, glycosuria, hyperglycemia, and insulin deficiency, as well as weight loss. For instance, the level of urine glucose (glycosuria) can be monitored with Testape (Eli Lilly, Indianapolis, Ind.) and plasma glucose levels can be monitored with a Glucometer 3 Blood Glucose Meter (Miles, Inc., Elkhart, Ind.) as described by Burkly, 1999, U.S. Ser. No. 5,888,507, herein incorporated by reference. Monitoring urine glucose and plasma glucose levels by these methods, NOD mice are considered diabetic after two consecutive urine positive tests gave Testape values of +1 or higher or plasma glucose levels >250 mg/dL (Burkly, 1999, supra). Another means of assaying diabetes in NOD mice is to examine pancreatic insulin levels in NOD mice. For example, pancreatic insulin levels can be examined by immunoassay and compared among treated and control mice (Yoon, U.S. Ser. No. 5,470,873, herein incorporated by reference). In this case, insulin is extracted from mouse pancreas and its concentration is determined by its immunoreactivity, such as by radioimmunoassay techniques, using mouse insulin as a standard (Yoon, supra).

In addition to monitoring NOD mice for diabetes in general, the effects of the inventive methods of treatment are also monitored for hedgehog-specific effects, thereby allowing a correlation to be drawn between expression of hedgehog and its effects on diabetes. For instance, if the hedgehog administered is sonic hedgehog (Shh), cells of the mouse pancreas are examined for the presence of Shh (to ensure its presence by the particular means used for administration) and the expression of the Shh receptor proteins patched and smoothened by immunohistochemistry, in a manner similar to that shown in FIG. 10. Immunohistochemistry is also be applied to examine the pancreatic β-cells of NOD mice for insulin, as in FIG. 10. The expression of patched and smoothened is further examined in NOD mouse islets by detection of the RNA transcript for the patched and smoothened receptors. Reverse transcription-polymerase chain reaction (RT-PCR) amplification is performed by known means to amplify a fragment of mouse patched or smoothened cDNA, and analyzed by agarose gel electrophoresis (as shown for patched in FIG. 11), according to standard means. The identification of the amplified cDNA fragment is confirmed as corresponding to the patched or smoothened RNA by Southern blot hybridization of the amplified fragment with a radiolabeled internal oligonucleotide probe for mouse patched or smoothened (as demonstrated for patched in FIG. 11), according to standard methods.

A number of animal models are useful for studying non-insulin-dependent diabetes mellitus (type 2) such as the rodent models the Zucker Diabetic Fatty (ZDF) rat, the Wistar-Kyoto rat, the diabetes (db) mouse, and the obese (ob) mouse (Pickup and Williams, eds, *Textbook of Diabetes*, 2nd Edition, Blackwell Science). The ZDF rat is widely used an animal model of diabetes mellitus type 2, as it displays numerous diabetic characteristics that are similar to those found in human diabetes mellitus type 2 (Clark et al., 1983, Proc. Soc. Exp. Biol. Med, 173:68). These diabetic characteristics include insulin resistance, impaired glucose tolerance, hyperglycemia, obesity, hyperinsulinemia, hyperlipidemia, and moderate hyertension. The diabetes of ZDF rats is genetically conferred and linked to the autosomal recessive fatty (fa) gene, such that ZDF rats are homozygous (fa/fa) for the fatty gene. ZDF rats typically develop the symptoms of diabetes between approximately 8–10 weeks of age, during which time β-cell failure and progression to overt diabetes occurs.

The ZDF rat is used as an animal model to test the effectiveness of the various methods of treatment of diabetes by administering hedgehog protein or gene. The treatments including administration of hedgehog protein, nucleic acids encoding a vector containing a hedgehog gene (gene therapy), cells expressing hedgehog protein, and tissue which produces hedgehog protein are therefore tested in the ZDF rat for their effect on type 2 diabetes.

The ZDF rat is administered hedgehog protein or gene, typically intraperitoneally, according to the following dosage amounts. For hedgehog protein, 2.5 mg protein/rat is administered. DNA encoding hedgehog is delivered in the amount of 20–200 ng episomal hedgehog vector/rat/day. For cell therapy, ZDF rats are administered about $5\times10^1$ to $5\times10^4$ cells per rat. Administration of hedgehog via hedgehog protein, hedgehog vector, or cell therapy is started in the ZDF rats at about 8 weeks of age, and is continued for 4 to 6 weeks. As noted above, gene therapy is administered daily, while protein and cell therapies are administered 3 times a week. To administer ZDF rats hedgehog via tissue that produces hedgehog protein, pancreatic tissue is removed from the rats at 4 weeks of age, transfected with about 0.1 to 1 ng hedgehog vector, and re-implanted after the allotted time required for the tissue to begin expressing hedgehog protein. The rats are monitored for diabetes beginning at about 10 weeks of age, being tested twice per week according to the methods described below. The effects of treatment are determined by comparison of treated and untreated ZDF rats, as well control Zucker lean (+/fa) rats that are not diabetic.

The effectiveness of the treatment methods of the invention on diabetes in the ZDF rats is monitored by assaying for diabetes in the ZDF rats by means known to those of skill in the art, including examining the ZDF rats for plasma glucose levels, plasma insulin levels, and weight gain. Plasma glucose levels are typically checked 1–2 times per week of hedgehog administration, and can be monitored with a Glucometer 3 Blood Glucose Meter (Miles, Inc., Elkhart, Ind.). Monitoring non-fasting plasma glucose levels by this methods, ZDF rats are considered diabetic when plasma glucose levels remain high (>250 mg/dL) or further increase, while effective treatment will cause rats to be non-diabetic, evidenced by a decrease in plasma glucose level (approximately 100–200 mg/dL) that is maintained during treatment (Yakubu-Madus et al., 1999, Diabetes, 48:1093). Non-fasting insulin levels can be monitored with a commercial radioimmunoassay kit (Diagnostic Products, Los Angeles, Calif.) with porcine and rat insulin as the standards (Yakubu-Madus, 1999, supra). In this assay, plasma insulin is monitored once per week and will remain at or above the starting level if treatment is effective against diabetes, but will decrease approximately 2–3 fold over four weeks in ZDF rats that remain diabetic. Additionally, fasting plasma glucose and insulin levels are determined after 4–6 weeks of hedgehog administration by performing an oral glucose tolerance test (OGTT) on rats that have been fasted overnight. In a typical OGTT, rats are given 2 g glucose/kg body weight animals by stomach gavage and blood samples are collected at 0, 10, 30, 60, 90, and 120 minutes and assayed (Yakubu-Madus, 1999, supra). In diabetic ZDF rats, fasting glucose values will increase from approximately 100–200 mg/dl at time zero to about 400–500 mg/dl at 30–60 minutes, and then decrease to about 350–450 mg/dl by 120 minutes. If diabetes is alleviated, fasting glucose plasma values will have a lesser initial decrease to about 200–250 mg/dl at 30–60 minutes, and then decrease to about 100–150 mg/dl by 120 minutes. Plasma insulin levels measured before and during an OGTT in fasting ZDF rats will typically double in value by 10 minutes, and then decrease back to the starting value for the remainder of the assay. In contrast, effective treatment of diabetes in ZDF rats is evidenced by a 4–5 fold increase in plasma insulin at 10 minutes, followed by a linear decrease to about the starting value at 90 minutes (Yakubu-Madus et al., 1999, supra). Another means of assaying diabetes in ZDF rats is to examine pancreatic insulin levels in ZDF rats. For example, pancreatic insulin levels can be examined by immunoassay and compared among treated and control rats, as described above for the NOD mouse animal model of diabetes.

In addition to examining the effects of hedgehog administration to ZDF rats for diabetes in general, the effects of the inventive methods of treatment are also monitored for hedgehog-specific effects (as described above for the Nod mouse animal model), thereby allowing a correlation to be drawn between expression of hedgehog and its effects on diabetes. In the case where the hedgehog administered to a ZDF rats is indian hedgehog (Ihh), cells of the rat pancreas are examined for the presence of Ihh and the expression of the Ihh receptor proteins patched and smoothened by immunohistochemistry. Similarly, the presence of insulin in the pancreatic β-cells of ZDF rats is also examined by immunohistochemistry. The expression of patched and smoothened is examined in ZDF rat islets by detection of the RNA transcript for the patched and smoothened receptors. Reverse transcription-polymerase chain reaction (RT-PCR) amplification is performed by known means to amplify a fragment of rat patched or smoothened cDNA, and analyzed by agarose gel electrophoresis (as shown for patched in FIG. 11), according to standard means. The identification of the amplified cDNA fragment is confirmed as corresponding to the patched or smoothened RNA by Southern blot hybridization of the amplified fragment with a radiolabeled internal oligonucleotide probe for rat patched or smoothened (as demonstrated for patched in FIG. 11), according to standard methods.

Hyperinsulinemia Treatment Methods According to the Invention

A method of the invention includes suppressing insulin secretion by inhibiting hedgehog protein through the administration of an inhibitor of hedgehog such as cyclopamine or derivatives thereof. In the administration of the hedgehog inhibitor, the inhibitor is delivered to the patient afflicted with hyperinsulinemia in an amount sufficient to provide an effective level of endogenous insulin in the patient. An "effective" or "normal" level of endogenous insulin in a patient refers generally to that level of insulin that is produced endogenously in a healthy patient, i.e., a patient who is not afflicted with hyperinsulinemia. Alternatively, an "effective" level may also refer to the level of insulin that is determined by the practitioner to be medically effective to alleviate the symptoms of hyperinsulinemia.

Dosage and Mode of Administration of Hedgehog Inhibitor According to the Invention Methods of the invention include administering an inhibitor of hedgehog, such as cyclopamine or a variant thereof. Thus, according to the invention, a hyperinsulinemic patient may be treated by administering to a patient afflicted with hyperinsulinemia cyclopamine, or a variant thereof. Optimally, the cyclopamine is administered in a pharmaceutically acceptable vehicle, and is administered in an amount sufficient to provide an effective level of endogenous insulin in the patient.

Various methods for administration may be employed. The cyclopamine formulation may be given orally, or may be injected intravascularly, subcutaneously, peritoneally, and so forth. The dosage of the therapeutic formulation will vary widely, depending upon the frequency of administration, the manner of administration, and the clearance of the agent from the patient. For example, the dose will range from 0.1 to 5 mg cyclopamine/kg body weight. The initial dose may be larger, followed by smaller maintenance doses. The dose may be administered as infrequently as weekly or biweekly, or fractionated into smaller doses and administered daily, semi-weekly, etc. to maintain an effective dosage level. In many cases, oral administration will require a higher dose than if administered intravenously.

The cyclopamine may be prepared as formulations at a pharmacologically effective dose in pharmaceutically acceptable media, for example normal saline, PBS, etc. The additives may include bacteriocidal agents, stabilizers, buffers, or the like.

Animal Models of Hyperinsulinemia

Treatments for hyperinsulinemia that result in relief of its symptoms are tested in an animal which exhibits symptoms of hyperinsulinemia, such that the animal will serve as a model for agents and procedures useful in treating hyperinsulinemia in humans. Potential treatments for hyperinsulinemia can therefore be first examined in the animal model by administering the potential treatment to the animal and observing the effects, and comparing the treated animals to untreated controls.

Hyperinsulinemia commonly occurs in animal models for diabetes mellitus type 2, such as the obese Zucker diabetic fatty (ZDF) rat, the KK rat, obese mouse (ob), and Wellesley hybrid mouse (Pickup and Williams, eds, *Textbook of Diabetes*, 2nd Edition, Blackwell Science). For instance, the ZDF rat experiences hyperinsulinemia, as exemplified by studies where 8 week old ZDF rats had nonfasting plasma insulin values that were 5–10 fold higher than their lean Zucker rat control littermates (Yakubu-Madus, 1999, supra). ZDF rats can therefore be used as an animal model for hyperinsulinemia.

The ZDF rat is administered cyclopamine, typically intraperitoneally, in dosage amounts of 1–10 mg/kg of body weight. Administration of cyclopamine is started in the ZDF rat at about 8 weeks of age and administered daily for 4 to 6 weeks. The effectiveness of the treatment methods of the invention on hyperinsulinemia in the ZDF rats is monitored by assaying for hyperinsulinemia by standard means. For example, plasma insulin levels of non-fasting rats can be monitored with a commercial radioimmunoassay kit (Diagnostic Products, Los Angeles, Calif.) with porcine and rat insulin as the standards (Yakubu-Madus, 1999, supra). In this assay, plasma insulin is monitored twice per week and is expected to decrease approximately 2–3 fold over four weeks in control ZDF rats, whereas effective treatment with cyclopamine is anticipated to cause a more dramatic decrease in plasma insulin of 5–10 fold or more. Another means of assaying hyperinsulinemia in ZDF rats is to examine pancreatic insulin levels in ZDF rats. For example, pancreatic insulin levels can be examined by immunoassay and compared among treated and control rats (Yoon, supra). For this assay, insulin is extracted from mouse pancreas and its concentration is determined by immunoreactivity, such as by radioimmunoassay techniques, using rat insulin as a standard.

EXAMPLES

The invention is illustrated by the following nonlimiting examples wherein the following materials and methods are employed. The entire disclosure of each of the literature references cited hereinafter are incorporated by reference herein.

Example I

Components of Hedgehog Signaling are Expressed in Mature Mouse Pancreatic β-Cells, Rat Islet Cells, and Rat INS-1 Cells Adult mouse pancreas was examined for the expression of the hedgehog receptor proteins patched and smoothened by immunohistochemistry. As shown in FIG. 10, the hedgehog receptor proteins patched (GenBank Accession No. U46155) (FIG. 10A) and smoothened (FIG. 10C) are expressed in the mouse pancreas islet. Patched and smoothened proteins are expressed in mouse pancreatic β-cells, located within the core of the islet, as demonstrated by their coexpression with insulin (FIGS. 10B, D). For immunohistochemistry, mouse pancreas was embedded in Tissue-Tek O.C.T. compound (Sakura Finetek, U.S.A., Inc., Torrance, Calif.) and frozen on dry ice. Tissue was sectioned at 7 micron increments and fixed for 5 minutes at room temperature in 4% paraformaldehyde in phosphate buffered saline. After multiple washes with phosphate buffered saline, tissue sections were blocked with 1% donkey serum followed by an overnight incubation at 4° C. with the indicated primary antisera. Specimens were then rinsed in phosphate buffered saline and incubated for one hour with secondary antisera as indicated. Specimens were mounted in fluorescence mounting medium (Kirekegaard and Perry Laboratories, Gaithersburg, Md.). Primary antisera utilized included goat polyclonal IgG anti-patched [Patched (G-19)], goat polyclonal IgG anti-smoothened [SMO (N-19)], each utilized at a 1:500 dilution (Santa Cruz Biotechnology, Inc., Santa Cruz, Calif.), and guinea pig polyclonal anti-insulin (1:300 dilution) (Linco Research, Inc., St. Charles, Mo.). Donkey anti-goat IgG Cy3 (1:1500 dilution) and donkey anti-guinea pig IgG Cy2 (1:500 dilution) (Jackson Immuno Research Laboratories, West Grove, Pa.) were used as secondary antisera. A Nikon Epifluorescence microscope equipped with an Optronics TEC-470 camera (Optronics Engineering, Goleta, Calif.) was used to capture images and interfaced with a Power Macintosh 7100 computer. Image processing and analyses were performed with IP Lab Spectrum (Signal Analytics Corp., Vienna, Va.) and Adobe Photoshop 4.0 (Adobe Systems Incorporated, San Jose, Calif.) software.

The rat insulinoma cell line INS-1, an established cell culture model of β-cells, was also shown to express components required for hedgehog signaling. INS-1 cells, provided by C. Wollheim (Asfari et al.,1992, Endocrinol.), were cultured in RPMI 1640 medium (2 g of glucose per liter) supplemented with 10% fetal bovine serum, 10 mM HEPES buffer, 1 mM sodium pyruvate, 100 U per ml penicillin G sodium, 100 μg per mL streptomycin sulfate, 0.25 μg per mL amphotericin B (GIBCO BRL Life Technologies, Inc., Gaithersburg, Md.), and 5 μl per liter β-mercaptoethanol (SIGMA, St. Louis, Mo.). For immunohistochemistry, INS-1 cells were grown in slide culture chambers (Nunc, Inc., Naperville, Ill.) prior to fixation in 4% paraformaldehyde in phosphate, buffered saline. As shown by immunohistochemistry, both patched (GenBank Accession No. AF079162) (FIG. 11A) and smoothened (GenBank Accession No. U84402) (FIG. 11C), known receptors for hedgehog, are coexpressed with insulin (FIGS. 11B,D) in INS-1 cells.

Figure 12:
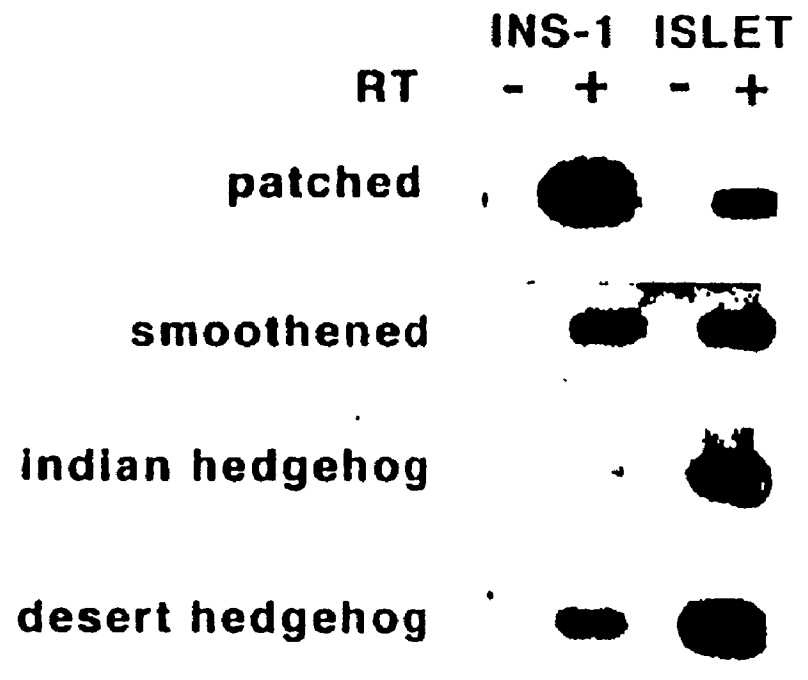

INS-1 cells, as well as rat islet cells, express patched and smoothened RNA, as demonstrated by reverse transcriptase-polymerase chain reaction (RT-PCR) amplification of the RNAs and detection by Southern blot analyses (FIG. 12). RT-PCR analysis was carried out as follows. For reverse transcription, RNA was isolated from cells and islets with Tri-Reagent (SIGMA, St. Louis, Mo.), using a modified guanidine thiocyanate and phenol purification method outlined in the manufacturer's protocol. For preparation of cDNA, total cellular RNA was preincubated with 50 ng/μl oligo(dT) 12–18 (GIBCO BRL Life Technologies, Inc., Gaithersburg, Md.) at 70° C. for 10 minutes and immediately chilled on ice. The addition of 0.5 U/μl RNAse Inhibitor, Cloned, 1X 1$^{st}$ strand buffer, 0.01 M dithiothreitol, 1 mM dATP, 1 mM dTTP, 1 mM dCTP, and 1 mM dGTP (GIBCO BRL Life Technologies, Inc., Gaithersburg, Md.) to the reaction was followed by a 2 minute incubation at 42° C. The final reaction was conducted with the addition of (RT+) Moloney murine leukemia virus reverse transcriptase (SuperScript 11 RT, GIBCO BRL Life Technologies, Inc., Gaithersburg, Md.) or (RT−) RNAse free water with a 60 minute incubation at 42° C. followed by a 15 minute incubation at 70° C. For PCR primers directed to nucleotides 390 to 656 of mouse patched (GenBank acc. no. U46155) were used as to amplify a 266 base pair fragment of rat patched as follows: forward primer, 5'-TCAGAAGATAGGAGAAGA-3' (SEQ ID No. 1), and reverse primer, 5'-TCCAAAGGTGTAATGATTA-3' (SEQ ID No 2). A 372 nucleotide fragment of rat smoothened cDNA was amplified with primers spanning nucleotides 386 to 758 of rat smoothened (GenBank acc. no. U84402) as follows: forward primer, 5'-TGCTGTGTGCTGTCTACAT-3' (SEQ ID No. 3) and reverse primer, 5'-AGGGTGAAGAGTGTACAGA-3' (SEQ ID No. 4). PCR amplifications were conducted for 30 to 35 cycles in a Perkin and Elmer 9600 Thermocycler with Taq DNA polymerase (TaKaRa, Takara Shuzo Co.

Following RT-PCR analysis, the identification of the amplified cDNA fragments from rat INS-1 and rat islet cells were confirmed as corresponding to the patched and smoothened RNAs by Southern blot hybridization of the amplified fragments with radiolabeled internal oligonucleotide probes directed against patched and smoothened (FIG. 12). The Southern blot analysis was performed by subjecting PCR products to agarose gel electrophoresis and staining with ethidium bromide for visualization and transferred to nylon membranes (Magnacharge, Micron Separations, Inc., Westboro, Mass.). Membranes were probed with a [$^{32}$P]-radiolabeled oligonucleotide probe according to the method of Southern (J. Mol. Biol., 1975). The following oligonucleotide probes were used: for patched, 5'-TACATG TATAACAGGCAATGGAAGTTGGAACATTTG-3' (SEQ ID No. 5) (targeted to nucleotides 529–564 of mouse patched cDNA (GenBank acc. no. U46155)), and for smoothened, 5'-CAAGAGCTGGTACGAGGACGTGGA-3' (SEQ ID No. 6) (targeted to nucleotides 621–644 of rat smoothened cDNA (GenBank acc. no. U84402)).

Figure 14:
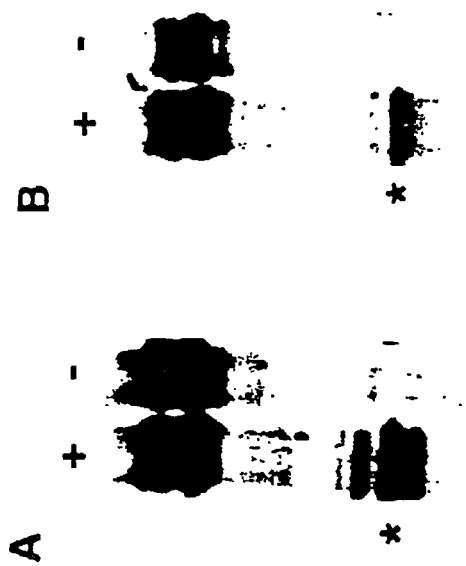
FIG. 14A shows results of immunoprecipitation (in the presence (+) or absence (−) of anti-Ihh serum) and Western immunoblot analysis of Ihh protein secreted from INS-1 cells.
FIG. 14B shows results of immunoprecipitation (in the presence (+) or absence (−) of anti-Dhh serum) and Western immunoblot analysis of Dhh protein secreted from INS-1 cells.

In addition to the hedgehog receptors, INS-1 cells express Ihh and Dhh proteins. As shown by immunohistochemistry in FIG. 13, INS-1 cells coexpress Ihh and Dhh with insulin. Immunohistochemistry was carried out as described above, using primary antisera that included goat polyclonal IgG anti-indian hedgehog carboxy terminus [Ihh (C-15)] and goat polyclonal IgG anti-desert hedgehog carboxy terminus [Dhh (M-20)] (Santa Cruz Biotechnology, Inc., Santa Cruz, Calif.). The presence of Ihh and Dhh in INS-1 cells is further demonstrated by immunoprecipitation and Western immunoblot analyses of Ihh and Dhh from media of cultured INS-1 cells (FIG. 14). For the immunoblot analysis, INS-1 cells were incubated in fresh culture medium for 24 hours before harvesting conditioned medium. Harvested medium was centrifuged at 2000 rpm for 2 minutes. For each immunoprecipitation reaction, 1.2 mL of the resulting supernatant was removed and precleared at 4° C. with Protein A-Sepharose (Pharmacia Biotech AB, Uppsala, Sweden) for 30 minutes. Precleared solutions were incubated at 4° C. in the presence or absence of polyclonal antisera, as, indicated. Antisera used for the immunoprecipitations included goat polyclonal IgG anti-indian hedgehog carboxy terminus [Ihh (C-15)] and goat polyclonal IgG anti-desert hedgehog carboxy terminus [Dhh (M-20)]. Immune complexes were precipitated by addition of Protein A-Sepharose, washed, and separated by SDS 12% polyacrylarnide gel electrophoresis. Western blot analysis was conducted as previously reported (Thomas et al., 1999, MCB) on PVDF membranes (Millipore) with primary goat polyclonal antisera as indicated and secondary anti-goat IgG-horseradish peroxidase conjugated antiserum (Santa Cruz Biotechnology, Inc., Santa Cruz, Calif.). Proteins were detected by chemiluminescence using ECL Western blotting reagents (Amersham Life Sciences, Arlington Heights, Ill.).

In accordance with the immunohistochemistry results, Ihh and Dhh RNA is expressed in INS-1 cells and rat islet cells, as demonstrated by RT-PCR that is detected by Southern blot analysis (FIG. 12). RT-PCR analysis was conducted as described above, in which a 387 nucleotide fragment of rat Ihh cDNA spanning nucleotides 22 to 409 of rat Ihh (GenBank acc. no. AF162914) was amplified using the following primers: forward primer, 5'-AGGACCGTCTGAACTCAC-3' (SEQ ID No. 7) and reverse primer, 5'-TTGCCATCTTCCCCCATG-3' (SEQ ID No. 8). To amplify a 331 nucleotide fragment of rat Dhh that spanned nucleotides 47 to 378 of rat Dhh (GenBank acc. no. AF148226), primers used were as follows: forward primer: 5'-GTTACGTGCGCAAGCA-3' (SEQ ID No. 9) and reverse primer: 5'-GCCTTCGTAGTGCAGT-3' (SEQ ID No. 10). Southern blot analyses were conducted as described above, using the following oligonucleotide probes: for Ihh, 5'-AACTGGGGAGCGTGTGGCCCTGTCAGC-3' (SEQ ID No. 11) (targeted to nucleotides 338–364 of rat Ihh cDNA (GenBank acc. no. AF162914)), and for Dhh, 5'-TAGTATGCCCGAGCGGACCCTT-3' (SEQ ID No. 12) (targeted to nucleotides 96–117 of rat Dhh cDNA (GenBank acc. no. AF148226)).

In the results described above, components involved in hedgehog signaling are detected in a rat β-cell line, rat islet cells, and mouse islet cells, indicating that hedgehog signaling functions in mature pancreatic β-cells.

Example II

Hedgehog Regulates Insulin Production

Figure 15:
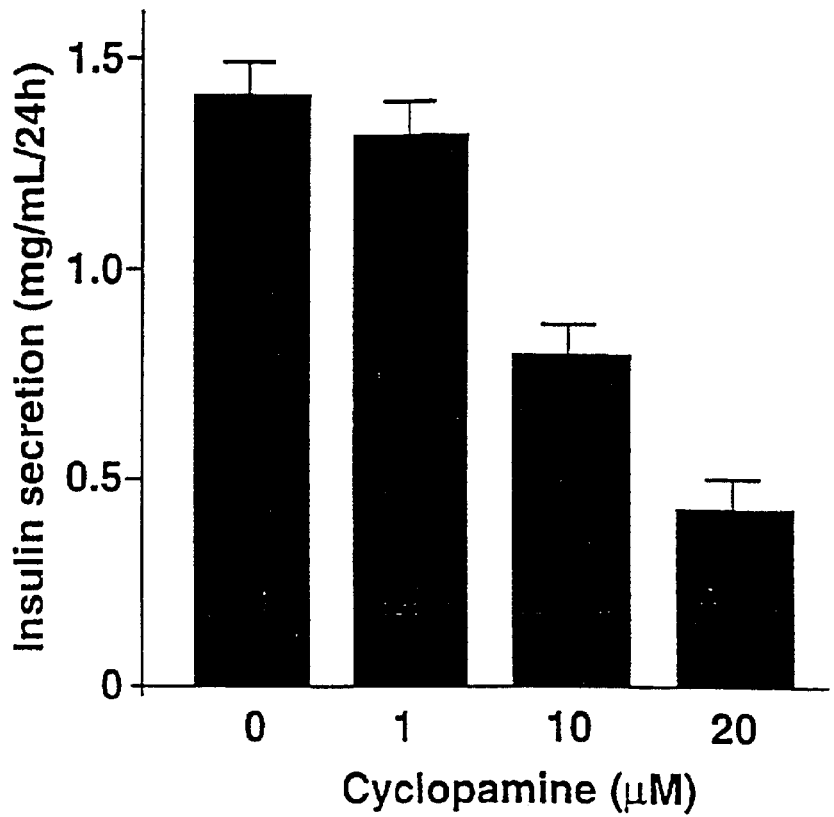
FIG. 15 shows results of inhibition of insulin secretion by cyclopamine in rat INS-1 cells that were cotransfected with a pEV control vector and an insulin promoter-reporter construct.
Figure 16:
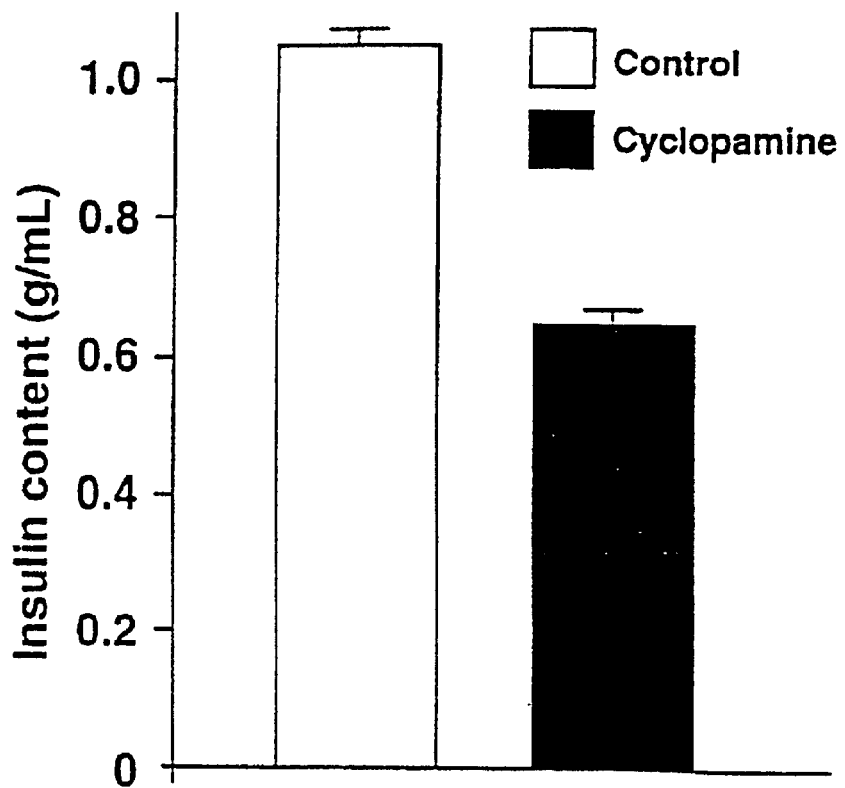
FIG. 16 shows results of treating rat INS-1 cells with cyclopamine.

The results described in Example I demonstrating that hedgehog proteins are expressed in the rat INS-1 cell line and rat islet cells, in conjunction with the demonstration that the hedgehog receptors patched and smoothened are expressed in rat INS-1 cells, rat islet cells, and mouse islet cells, suggest that hedgehog could play a role in the production of insulin by pancreatic β-cells. This potential role was examined with the rat INS-1 cell line, which intrinsically expresses Ihh and Dhh proteins (FIGS. 13 and 14). The cells were treated with the small molecule cyclopamine, a cholesterol derivative that has been shown to inhibit the attachment of the appropriate cholesterol to Shh, thus rendering Shh deficient for signaling (Kim and Melton, 1998, PNAS 95:13036). Cyclopamine was administered to INS-1 cells that were transiently transfected, according to standard means, with an empty vector pEV control and an insulin promoter-reporter construct. Cyclopamine (gift of W. Gaffield, USDA, Albany, Calif.) was prepared as a stock solution of 10 mM in 95% ethanol. Insulin secretion was assessed after 24 hours of cell exposure to cyclopamine by measuring the concentration of insulin in the media. As shown in FIG. 15, addition of cyclopamine in the cellular growth medium had a dose-dependent effect on insulin secretion in INS-1 cells, such that increasing amounts of cyclopamine increasingly inhibited insulin secretion, indicating that hedgehog acts to stimulate insulin production in these cells. Insulin levels were measured with a Rat Insulin RIA Kit (LINCO Research, Inc., St. Louis, Mo.) using the protocol outlined by the manufacturer. For determination of insulin secretion rates, fresh culture medium, to which cyclopamine in 0.2% ethanol or 0.2% ethanol vehicle was added as indicated, was applied to cultured INS-1 cells. After 24 hours of incubation, 500 µL aliquots of culture medium were removed and serially diluted for the assay. Culture medium that was not exposed to cells was tested as a negative control for the assay. In some experiments, transfected cells were assessed for insulin secretion rates. In these experiments, after incubation with lipofectamine and DNA, the transfected cells received fresh culture medium and 24-hour insulin secretion rates were assessed. Given that the cells intrinsically express hedgehog, the cells were also treated with cyclopamine in the absence of any transfection. As shown in FIG. 16, INS-1 cells treated for 24 hours with 20 μM cyclopamine had a 40% reduction in cellular insulin content. To determine cellular insulin content, INS-1 cells were incubated for 24 hours with fresh culture medium and cyclopamine in 0.2% ethanol or 0.2% ethanol vehicle, as indicated. Cells were then rinsed in phosphate buffered saline and lysed in 0.1N HCl in 100% ethanol at 4° C. The lysate was incubated overnight at −70° C. The thawed lysate was vortexed and subjected to brief centrifugation at 14,000 rpm. The resulting supernatant was dried under vacuum, resuspended in 200 mL Assay buffer, and serially diluted for insulin measurements with the Rat Insulin RIA Kit.

Figure 17A:
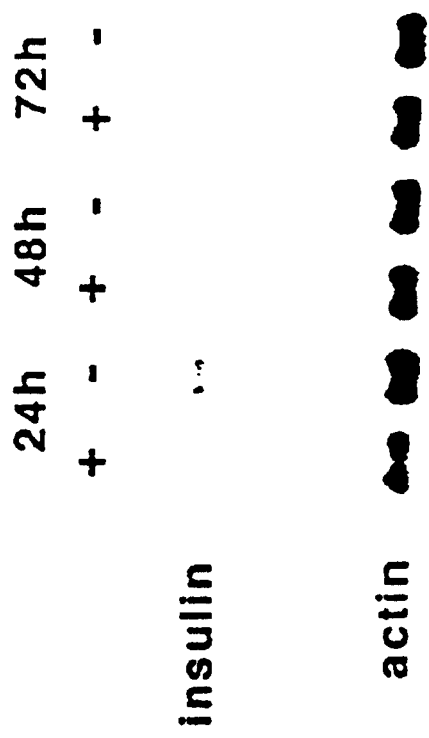
FIG. 17A shows a Northern blot of insulin mRNA levels in INS-1 cells in response to cyclopamine.
Figure 17B:
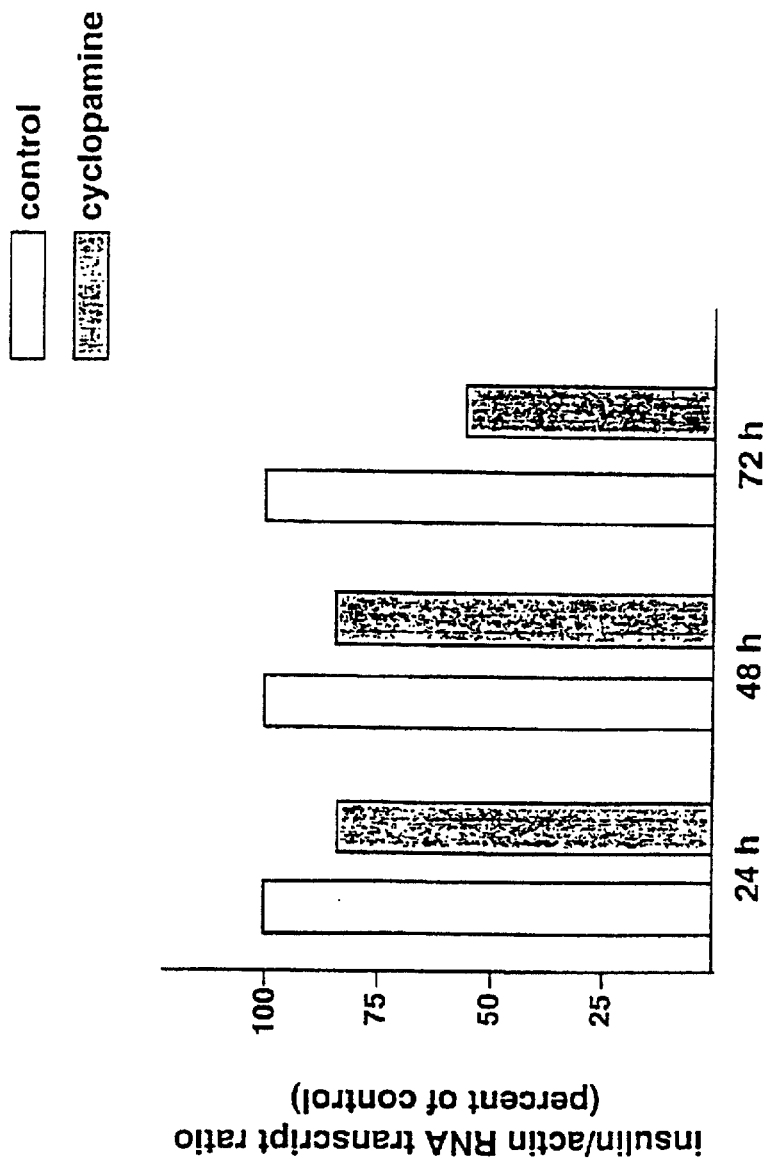
FIG. 17B shows quantitation of the results in 17A.

The decrease in cellular insulin content of INS-1 cells in response to cyclopamine was accompanied by a decrease in the levels of insulin mRNA, as shown by Northern RNA blots in FIG. 17. For the Northern analysis, subconfluent INS-1 cells were incubated with 20 μM cyclopamine in 0.2% ethanol or 0.2% ethanol vehicle for the times indicated. For isolation of total RNA, cells were washed in phosphate buffered saline and lysed with Tri-Reagent (SIGMA, St. Louis, Mo.). Total cellular RNA was prepared according to the manufacturer's protocol. For each sample, 4 μg total RNA was separated by electrophoresis on a denaturing gel consisting of 1×MOPS, 1.2% agarose and 1% formaldehyde. Samples were transferred using standard methods (Ausubel et al., Short Protocols in Molecular Biology, Third Edition, John Wiley and Sons, Inc., 1995.) to nylon membranes (Hybond-N+, Amersham Pharmacia Biotech, Inc., Piscataway, N.J.) and crosslinked with ultraviolet light (UV Stratalinker 1800, Stratagene, La Jolla, Calif.). The membranes were prehybridized in Rapid-Hyb Buffer (Amersham Pharmacia Biotech, Inc.) prior to hybridization for 4 hours at 65° C. with radiolabeled probes. Insulin transcripts were probed with a 231 nucleotide fragment (spanning nucleotides 349 to 580 of the rat insulin I gene, Genbank acc. no. V01242) of rat insulin I cDNA. Actin transcripts were probed with a 630 nucleotide cDNA fragment of rat β-actin cDNA (beginning with nucleotide 262 and ending with nucleotide 2371 derived from the rat beta-actin gene, Genbank acc. no. V01217). Probes were labeled with [$\alpha$-$^{32}$P]-dATP using the RadPrime DNA Labeling System (GIBCO BRL Life Technologies, Inc., Gaithersburg, Md.). Blots were rinsed in a solution of 0.1×SSC with 0.1% SDS at room temperature and 55° C. prior to autoradiography. For quantitation, autoradiograms were scanned with a Computing Densitometer (Molecular Dynamics, Sunnyvale, Calif.) and individual band intensities were determined with ImageQuant software (Molecular Dynamics, Sunnyvale, Calif.). These studies of insulin production in INS-1 cells indicate that hedgehog signaling regulates the production of insulin in INS-1 cells.

Figure 18:
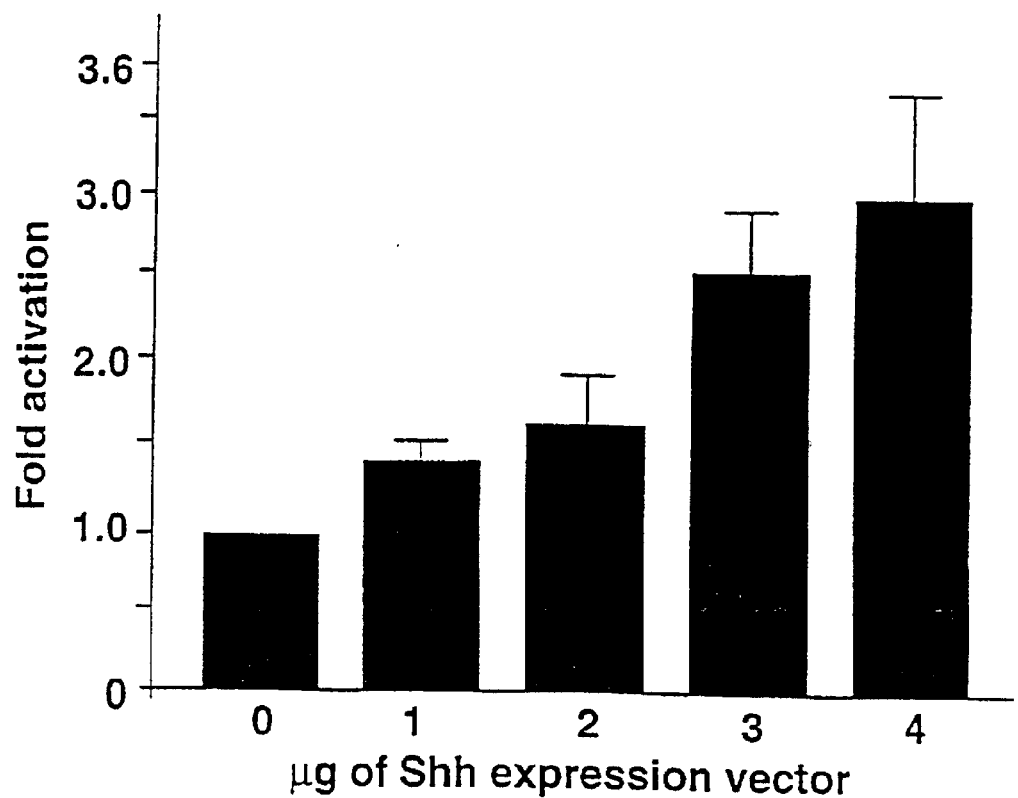
FIG. 18 shows results of transcriptional activation of a rat insulin I promoter construct in which rat INS-1 cells were cotransfected with an expression vector encoding sonic hedgehog (pShh) and a luciferase reporter construct (−410 INS-luc) containing portions of the rat insulin I 5' flanking region.
Figure 19:
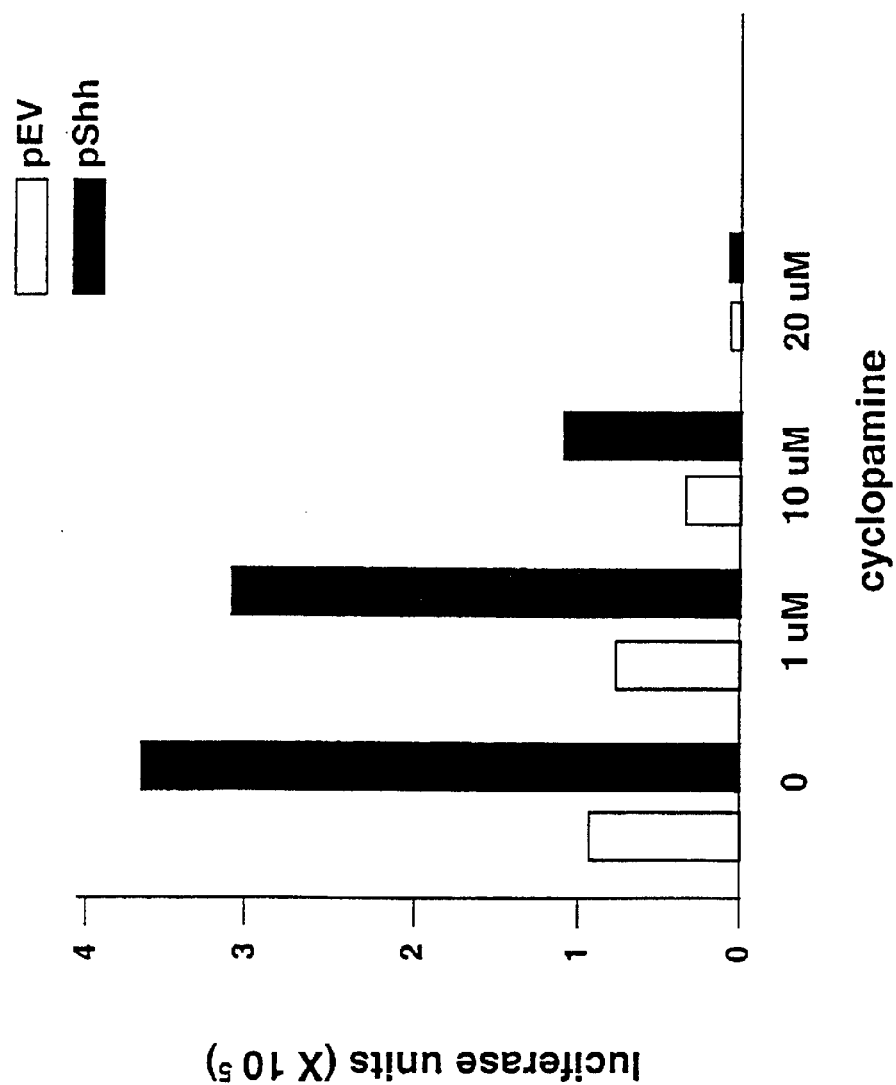
FIG. 19 shows results of inhibition of transcriptional activation of a rat insulin I promoter construct by cyclopamine in which rat INS-1 cells were cotransfected with an expression vector encoding sonic hedgehog (pShh) and a luciferase reporter construct (−410 INS-luc) containing portions of the rat insulin I 5' flanking region, and a luciferase reporter construct (−410 INS-luc) containing portions of the rat insulin I 5' flanking region.

To determine whether hedgehog regulation of insulin production occurs at the transcriptional level, INS-1 cells were transiently transfected with 5–6 μg total DNA and 10 μL Lipofectamine according to the manufacturer's instructions (GIBCO BRL Life Technologies, Inc., Gaithersburg, Md.) with increasing concentrations of Shh expression vector pSHH in the presence of a rat insulin I promoter-reporter construct −410 INS-luc. The full length cDNA for mouse sonic hedgehog was a gift from A. McMahon, and pSHH plasmid was constructed by subcloning mouse sonic hedgehog into a pED expression vector (Kaufman et al., NAR 19:4485, 1991) obtained from C. Miller. The plasmid −410 INS-LUC consists of a fragment of the rat insulin I gene promoter that spans nucleotides −410 to +49 inserted into the pXP2 vector that includes firefly luciferase reporter sequences (Lu, M., et al, 1997, J. Biol. Chem.: 272:28349). As assayed by the activity of the luciferase gene encoded on the insulin I promoter-reporter construct, Shh increased insulin promoter activity in a dose-dependent manner, up to 2.5-fold (FIG. 18). For luciferase assays, cells were harvested 24 hours after transfection with IX Reporter Lysis Buffer (Promega, Madison, Wis.). Luciferase assays were conducted with the Luciferase Assay System as outlined by the manufacturer (Promega, Madison, Wis.). Luciferase activities were normalized for extract protein concentrations as determined by the Bio-Rad Protein Assay (Bio-Rad Laboratories, Hercules, Calif.), a modified Bradford assay (Bradford, M., 1976, Anal. Biochem., 72:248). These results demonstrate that Shh stimulates insulin production in pancreatic β-cells, and that it does so by stimulating insulin gene expression at the level of transcription. In a related observation, cyclopamine was shown to inhibit the Shh-mediated activation of the insulin promoter. In the absence of the Shh expression construct, cyclopamine inhibited the basal insulin promoter activity of INS-1 cells in a dose-dependent manner, inhibiting the promoter by up to 90 percent (FIG. 19). These data demonstrate the ability of Shh to activate the insulin promoter. Further, they indicate that INS-1 cells utilize the Shh signaling pathway to maintain insulin promoter activity.

Example III

Hedgehog Regulates the Expression of IDX-1 in Differentiated β-cells

In addition to regulating the expression of the insulin gene, Shh was found to regulate the expression of the IDX-1 gene (GenBank Accession No. U04833), which in turn could be responsible, at least in part, for the stimulation of the insulin gene in pancreatic β-cells by Shh. The IDX-1 protein is a transcription factor that is also useful for treating diabetes (Habener et al., U.S. Ser. No. 5,858,973). The IDX-1 (also referred to as PDX-1/IPF-1/STF-1) protein activates the transcription of the insulin gene of the insulin gene by interacting on a DNA-control sequence known as Far-Flat, which is located in the promoter region of the insulin gene. IDX-1 is essentially required for pancreas development, as the targeted disruption of the PDX-1 gene in mice (IDX-1 in rat nomenclature) results in failure of the pancreas to develop. The corresponding disruption of the expression of the human IPF-1 gene (IDX-1 in rat nomenclature) also results in failure of the pancreas to develop.

Figure 20:
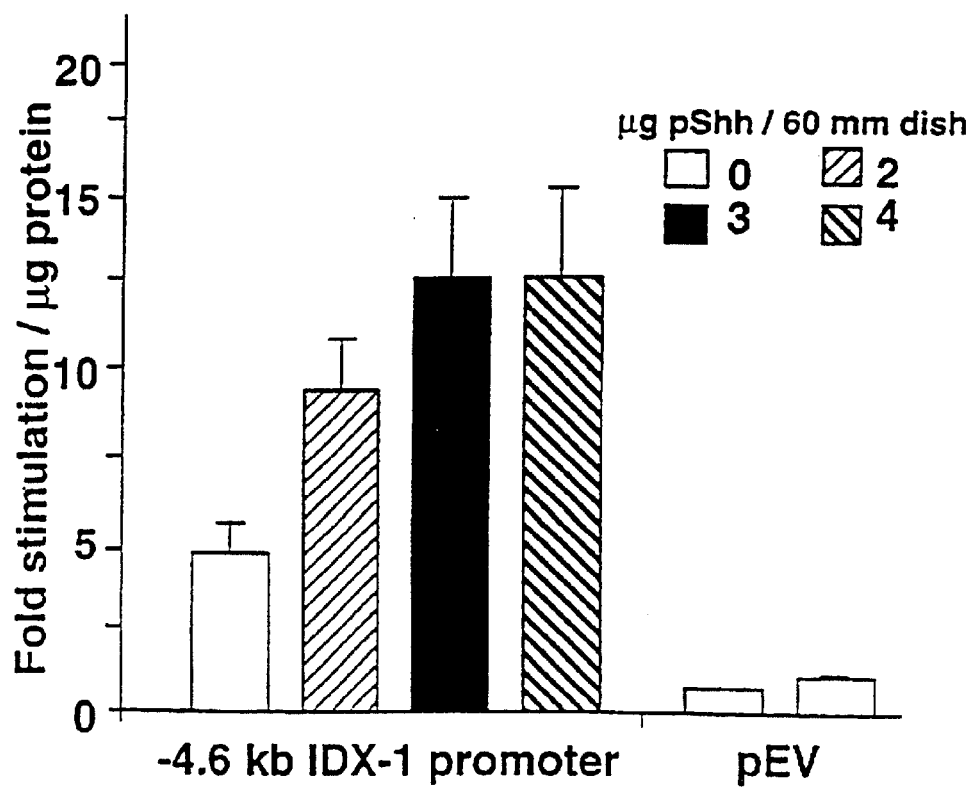
FIG. 20 shows transcriptional activation of IDX-1 promoter constructs by sonic hedgehog in which rat INS-1 cells were cotransfected with an expression vector encoding sonic hedgehog (pShh) and an IDX-1 reporter construct containing portions IDX-1 5' flanking region.
Figure 21:
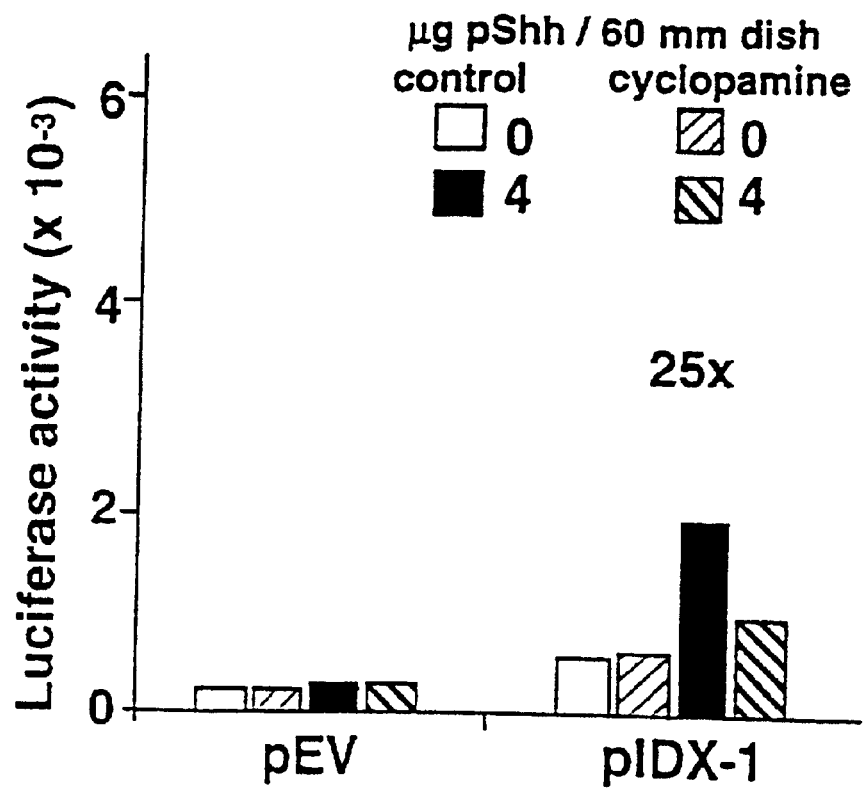
FIG. 21 shows cyclopamine inhibition of transcriptional activation of IDX-1 promoter constructs by sonic hedgehog in which rat INS-1 cells were cotransfected with an expression vector encoding sonic hedgehog (pShh) and an IDX-1 reporter construct containing portions IDX-1 5' flanking region.

The ability of Shh to regulate IDX-1 expression is shown in FIG. 20, where transient transfections of rat insulinoma INS-1 cells with an expression plasmid for Shh increases transcription of a −4.6 kb mouse IDX-1 promoter activity in a dose-dependent manner. In this assay, INS-1 cells were transiently transfected with 2 μg −4.6IDX-pGL3 (−4.6 kb IDX-1 promoter) and 0, 2, 3, or 4 μg pSHH with 4, 2, 1, or 0 μg pED empty vector, respectively, as indicated. Alternatively, cells were transfected with 2 μg, pGL3 (pEV) and 0 or 4 μg pSHH with 4 or 0 μg pED empty vector, respectively, as indicated. Cells were harvested after 24 hours. Luciferase activity was normalized to extract protein concentrations. Fold stimulation was determined by normalizing luciferase units per μg protein for each transfection data point to the activity of pGL3 empty vector in the presence of 4 μg pED empty vector, designated an activity of 1. In addition, co-transfection of INS-1 cells with an expression plasmid for Shh and a mouse IDX-1 promoter-reporter construct showed an increase in luciferase activity with the addition of the Shh expression plasmid compared to the luciferase activity obtained with transfection of the insulin I promoter-reporter construct by itself (FIG. 21). For this assay, INS-1 cells were transiently transfected with 2 μg −4.6IDX-pGL3 (pIDX-1) or pGL3 (pEV) and 4 μg pED empty vector (0) or 4 μg pSHH (4), as indicated. Approximately 90 minutes prior to transfection, cells were pretreated with 0.2% ethanol (control), or 10 μM cyclopamine in 0.2% ethanol (cyclopamine) in serum free medium. At the time of transfection, 0.2% ethanol (control) or 10 μM cyclopamine in 0.2% ethanol (cyclopamine) was added to the final transfection cocktail. After five hours of incubation with the transfection cocktail, the transfection cocktail was removed and cells were incubated in INS-1 culture medium with 0.19% ethanol (control) or 10 μM cyclopamine in 0.2% ethanol (cyclopamine) for an additional 24 hours prior to harvest. Luciferase activities of harvested extracts are shown in FIG. 21. The −4.61DX-pGL3 plasmid was constructed by inserting a −4.6 kb mouse IDX-1 promoter fragment (Stoffers et al., 1999, Endocrinology 140:5374) into a blunted Hind III restriction site of the pGL3-Basic Vector (Promega Life Sciences, Madison, Wis.). Furthermore, administration of the Shh inhibitor cyclopamine decreases Shh-mediated activation of the IDX-1 promoter (FIG. 21). The regulation of IDX-1 expression by Shh suggests that Shh stimulates insulin production in adult pancreatic β-cells, as least in part, by stimulating expression of the IDX-1 gene.

Example IV

Hedgehog Stimulates the Neogenesis of β-cells from Pancreatic Ductal Precursor Cells The ability of hedgehog to regulate the expression of the IDX-1 gene indicates that hedgehog may also stimulate β-cell growth and differentiation from the β-cell progenitor cells that reside in the pancreatic ducts of the adult pancreas. The process of the differentiation of new adult, pancreatic β-cells from ductal precursor cells is referred to as β-cell neogenesis. The IDX-1 transcription factor has been strongly implicated in stimulating β-cell neogenesis by several lines of evidence. In mice, β-cell neogenesis is known to occur for as long as 3 weeks postnatally (Sander and German, 1997, J. Mol. Med. 75:327). Inactivation of the IDX-1 gene in the pancreatic β-cells of mice that primarily occurred postnatally correlated with an approximately 40% decrease in adult pancreatic β-cells (Ahlgren et al., 1998, Genes. Dev. 12:1763), suggesting a role for IDX-1 protein in β-cell neogenesis. The insulinotropic hormone, glucagon-like peptide-1 (GLP-1) and GLP-1 agonists such as exendin-4 stimulate neogenesis (Gang et al., 1999, Diabetes 48:2270), and GLP-1 and exendin-4 stimulate the expression of IDX-1 in the pancreas (Stoffers et al., Diabetes, in revision; Wang et al., 1999, Endocrinol. 140:4904), indicating that IDX-1 stimulates β-cell neogenesis. In addition, in the partial pancreatectomy rate model of diabetes mellitus type 2, IDX-1 expression is markedly increased in the early regenerative phase in which neogenesis is stimulated (Sharma et al., 1999, Diabetes 48:507). Given the role of IDX-1 expression in β-cell neogenesis, stimulation of IDX-1 expression will correspond with stimulation of β-cell neogenesis. As described above and shown in FIG. 20 and FIG. 21, hedgehog stimulates the IDX-1 promoter and therefore, IDX-1 expression. Thus, hedgehog protein can stimulate β-cell neogenesis from precursor ductal cells of the pancreas through stimulation of IDX-1 protein in those cells.

Example V

Suppression of Insulin Secretion and β-cell Neogenesis with an Inhibitor of Hedgehog The ability of hedgehog to stimulate insulin production as described above in Example II was evidenced in part by the ability of an inhibitor of hedgehog, the steroidal alkaloid cyclopamine, to cause a decrease in the production of insulin by the rat insulinoma cell line INS-1, a cell culture model of β-cells. Cyclopamine or a similar inhibitor of hedgehog signaling could therefore be useful in suppressing production of insulin by pancreatic β-cells in those instances where it would advantageous to do so, for example, in patients afflicted with hyperinsulinemia. Treatment of INS-1 cells with cyclopamine resulted in a dose-dependent reduction in insulin secretion by the cells (FIG. 15). Furthermore, treatment of INS-1 cells with cyclopamine caused a 40% reduction in the cellular content of insulin (FIG. 16). Cyclopamine was also shown to inhibit the transcription of the insulin gene in INS-1 cells (FIGS. 17 and 19). These results suggest that cyclopamine could be used to suppress insulin production and secretion in pancreatic β-cells.

In addition to suppressing insulin secretion by β-cells, the hedgehog inhibitor cyclopamine could be applied to suppress growth of pancreatic β-cells as a means of treatment of hyperinsulinemia. As described above in Example IV, hedgehog protein can stimulate β-cell neogenesis from precursor ductal cells of the pancreas through stimulation of IDX-1 expression in those cells. The cholesterol derivative cyclopamine inhibits the attachment of the appropriate cholesterol to hedgehog, thus rendering hedgehog deficient for signaling (Kim and Melton, 1998, supra) as evidenced by the effects of cyclopamine on hedgehog signal transduction in development (for example, Kim and Melton, 1998, supra) and the regulation of insulin production in INS-1 cells (as described above). Inhibition of hedgehog with cyclopamine is therefore likely to inhibit hedgehog signaling that stimulates IDX-1 production in precursor ductal cells. The resultant decrease in IDX-1 expression will in turn correspondingly cause a decrease in stimulation of β-cell neogenesis, thereby suppressing growth of pancreatic β-cells.

Example VI

Treatment of Hyperinsulinemia Conditions with Inhibitors of Hedgehog

Cyclopamine has been shown to inhibit hedgehog signaling and affect insulin production in rat INS-1 cells, as demonstrated by a decrease in insulin content (FIG. 18) and insulin secretion (FIG. 17), along with inhibition of insulin gene expression (FIGS. 17 and 19). The ability to suppress hedgehog with cyclopamine suggests that cyclopamine or related inhibitors of hedgehog may be useful for the treatment of hyperinsulinemia, since the hedgehog inhibitors will cause a decrease in insulin production by pancreatic β-cells. Furthermore, inhibitors of hedgehog are anticipated to suppress β-cell growth, as described above in Example V. Conditions of hyperinsulinemia that could be treated by inhibitors of hedgehog include but are not limited to hyperinsulinemia caused by insulinomas or mutations in the subunits of the sulfonylurea receptor on β-cells, Kir6.2 and SUR-1 (Lonlay-Debeney et al., 1999, New Engl. J. Med., 340:1169). Such mutations cause severe neonatal hypoglycemia, referred to as congenital hyperinsulinemia, persistent hyperinsulinemia and hypoglycemia of infancy (PHHI), or familial hyperinsulinemia and hypoglycemia of infancy (FHHI).

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims.

What is claimed is:

1. A method of treating deficiency of insulin in a patient, comprising administering to a patient in need thereof a nucleic acid encoding hedgehog protein, said hedgehog protein being one of desert hedgehog, indian hedgehog, or sonic hedgehog, in an amount effective to raise the level of insulin in said patient.

2. The method of claim 1, wherein said patient is afflicted with diabetes.

* * * * *